(12) United States Patent
Tweten et al.

(10) Patent No.: US 7,179,888 B2
(45) Date of Patent: Feb. 20, 2007

(54) **ANTIGENIC, NON-TOXIC MUTANTS OF *CLOSTRIDIUM SEPTICUM* ALPHA TOXIN AND VACCINES, ANTIBODIES, SERA, AND METHODS OF TREATMENT THEREWITH**

(75) Inventors: Rodney K. Tweten, Edmond, OK (US); Jody Melton, Alva, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 623 days.

(21) Appl. No.: 10/194,489

(22) Filed: Jul. 10, 2002

(65) Prior Publication Data
US 2003/0086946 A1   May 8, 2003

Related U.S. Application Data

(60) Provisional application No. 60/305,725, filed on Jul. 16, 2001, provisional application No. 60/304,527, filed on Jul. 11, 2001.

(51) Int. Cl.
*C07K 14/33* (2006.01)
(52) U.S. Cl. .................... 530/350; 424/247.1
(58) Field of Classification Search ............ 424/247.1; 530/350
See application file for complete search history.

(56) References Cited

FOREIGN PATENT DOCUMENTS

WO   PCT/US02/21900   6/2003

OTHER PUBLICATIONS

Dictionary of Biochemistry and Molecular Biology, Stenesh, 1989.*
McGuiness et al., Mol. Microbiol. 7:505-514, 1993.*
McGuiness et al. Lancet 337:514-517, 1991.*
Houghten et al., New Approaches to Immunization, Vaccines86, Cold Spring Harbor Laboratory, 1986, p. 21-25.*
Ellis Chapter 29 of Vaccines, Plistkin, et al. (eds) WB Saunders, Philadelphia, 1998.*
Gordon et al., Infect. Immun., 65:4130-4134, 1997.*
Harlow et al., Antibodies, a laboratory manual, Cold Spring Harbor Laboratory, USA, 1988, pp. 56, 96-97, 141.*
Ballard et al., "The Primary Structure of *Clostridium septicum* Alpha-Toxin Exhibits Similarity with That of *Aeromonas hydrophila* Aerolysin", Infection and Immunity, Jan. 1995, pp. 340-344.
Gordon et al., "*Clostridium septicum* Alpha Toxin Uses Glycosylphosphatidylinositol-anchored Protein Receptors", The Journal of Biological Chemistry, vol. 274, No. 38, Issue of Sep. 17, 1999, pp. 27274-27280.
Sellman et al., "Generation of a membrane-bound, oligomerized pre-pore complex is necessary for pore formation by *Clostridium septicum* alpha toxin", Molecular Microbiology, 1997, 23(3), pp. 551-558.
Sellman et al., "The propeptide of *Clostridium septicum* alpha toxin functions as an intramolecular chaperone and is a potent inhibitor of alpha toxin-dependent cytolysis", Molecular Microbiology, 1997, 25(3), pp. 429-440.
Ho et al., "Site-directed mutagenesis by overlap extension using the polymerase chain reaction" Elsevier Science Publisher B.V. (Biomedical Division), 1989, pp. 51-59.
Ballard et al., "Purification and Characterization of the Lethal Toxin (Alpha-Toxin) of *Clostridium septicum*", Infectioin and Immunity, Mar. 1992, vol. 60, No. 3, pp. 784-790, see entire document.
Nagahama et al., "Site-Directed Mutagenesis of Histidine Residues in *clostridium perfringens* Alpha-Toxin", Journal of Bacteriology, Mar. 1995, vol. 177, No. 5, pp. 1179-1185, see entire document.
Riddell et al., "Isolation of a genomic fragment encoding hemolytic activity from *Clostridium septicum*", Abtracts of the General Meeting of the American Society for Microbiology, 1994, vol. 94, p. 49, see entire abstract, No. B-115.
Schoepe et al., "Naturally Occurring *Clostridium perfringens* Nontoxic Alpha-Toxin Variant as a Potential Vaccine Candidate against Alpha-Toxin-Associated Diseases", Infection and Immunity, Nov. 2001, vol. 69, No. 11, pp. 7194-7196, see entire document.

* cited by examiner

Primary Examiner—Robert A. Zeman
Assistant Examiner—Brian J. Gangle
(74) Attorney, Agent, or Firm—Dunlap, Codding & Rogers, P.C.

(57) ABSTRACT

A vaccine utilizing purified mutant alpha toxins from *Clostridium septicum* for humans and animals against infections caused by *C septicum*. Persons potentially affected by *C. septicum* infections include colonic cancer patients, diabetics, leukemia patients, and neutropenics. The alpha toxin mutant of the vaccine lacks the toxicity of a native *C. septicum* alpha toxin. A serum comprising antibodies raised to the alpha toxin mutant is also available for treating humans or animals against *C. septicum* infections. The serum may be used in a method for conferring passive immunity against *C. septicum*. Antibodies to the alpha toxin mutant may be used in diagnostic tests or in treatments to clear alpha toxin from bodily fluids. The mutant alpha toxin may be produced by recombinant methods using cDNA encoding the toxin, the cDNA contained for example in a plasmid or host cell.

1 Claim, No Drawings

SEQUENCE LISTING

<160> NUMBER OF SEQ ID NOS: 23

<210> SEQ ID NO 1
<211> LENGTH: 411
<212> TYPE: PRT
<213> ORGANISM: Clostridium septicum

<400> SEQUENCE: 1

```
Thr Asn Leu Glu Glu Gly Gly Tyr Ala Asn His Asn Asn Ala Ser Ser
1               5                   10                  15

Ile Lys Ile Phe Gly Tyr Glu Asp Asn Glu Asp Leu Lys Ala Lys Ile
            20                  25                  30

Ile Gln Asp Pro Glu Phe Ile Arg Asn Trp Ala Asn Val Ala His Ser
        35                  40                  45

Leu Gly Phe Gly Trp Cys Gly Gly Thr Ala Asn Pro Asn Val Gly Gln
    50                  55                  60

Gly Phe Glu Phe Lys Arg Glu Val Gly Ala Gly Gly Lys Val Ser Tyr
65                  70                  75                  80

Leu Leu Ser Ala Arg Tyr Asn Pro Asn Asp Pro Tyr Ala Ser Gly Tyr
                85                  90                  95

Arg Ala Lys Asp Arg Leu Ser Met Lys Ile Ser Asn Val Arg Phe Val
            100                 105                 110

Ile Asp Asn Asp Ser Ile Lys Leu Gly Thr Pro Lys Val Lys Lys Leu
            115                 120                 125
```

```
Ala Pro Leu Asn Ser Ala Ser Phe Asp Leu Ile Asn Glu Ser Lys Thr
        130                 135                 140

Glu Ser Lys Leu Ser Lys Thr Phe Asn Tyr Thr Thr Ser Lys Thr Val
145                 150                 155                 160

Ser Lys Thr Asp Asn Phe Lys Phe Gly Glu Lys Ile Gly Val Lys Thr
                165                 170                 175

Ser Phe Lys Val Gly Leu Glu Ala Ile Ala Asp Ser Lys Val Glu Thr
            180                 185                 190

Ser Phe Glu Phe Asn Ala Glu Gln Gly Trp Ser Asn Thr Asn Ser Thr
        195                 200                 205

Thr Glu Thr Lys Gln Glu Ser Thr Thr Tyr Thr Ala Thr Val Ser Pro
    210                 215                 220

Gln Thr Lys Lys Arg Leu Phe Leu Asp Val Leu Gly Ser Gln Ile Asp
225                 230                 235                 240

Ile Pro Tyr Glu Gly Lys Ile Tyr Met Glu Tyr Asp Ile Glu Leu Met
                245                 250                 255

Gly Phe Leu Arg Tyr Thr Gly Asn Ala Arg Glu Asp His Thr Glu Asp
            260                 265                 270

Arg Pro Thr Val Lys Leu Lys Phe Gly Lys Asn Gly Met Ser Ala Glu
        275                 280                 285

Glu His Leu Lys Asp Leu Tyr Ser His Lys Asn Ile Asn Gly Tyr Ser
    290                 295                 300

Glu Trp Asp Trp Lys Trp Val Asp Glu Lys Phe Gly Tyr Leu Phe Lys
305                 310                 315                 320

Asn Ser Tyr Asp Ala Leu Thr Ser Arg Lys Leu Gly Ile Ile Lys
                325                 330                 335

Gly Ser Phe Thr Asn Ile Asn Gly Thr Lys Ile Val Ile Arg Glu Gly
            340                 345                 350

Lys Glu Ile Pro Leu Pro Asp Lys Lys Arg Gly Lys Arg Ser Val
        355                 360                 365

Asp Ser Leu Asp Ala Arg Leu Gln Asn Glu Gly Ile Arg Ile Glu Asn
    370                 375                 380

Ile Glu Thr Gln Asp Val Pro Gly Phe Arg Leu Asn Ser Ile Thr Tyr
385                 390                 395                 400

Asn Asp Lys Lys Leu Ile Leu Ile Asn Asn Ile
                405                 410

<210> SEQ ID NO 2
<211> LENGTH: 1233
<212> TYPE: DNA
<213> ORGANISM: Clostridium septicum

<400> SEQUENCE: 2
acaaatcttg aagaggggggg atatgcaaat cataataatg cttcttcaat taaaatattt    60
ggatatgaag acaatgaaga tttaaaagct aaaattattc aagatccaga gtttataaga   120
aattgggcaa atgtagctca ttcattagga tttggatggt gcggtggaac ggctaatcca   180
aacgttggac aaggttttga atttaaaaga gaagttgggg caggtggaaa agtatcttat   240
ttattatctg ctagatacaa tccaaatgat ccttatgcaa gtggatatcg tgcaaaagat   300
agactttcta tgaaaatatc aaatgttaga tttgttattg ataatgattc tataaaatta   360
ggtacaccta agtgaaaaaa attagcacct ttaaactctg ctagttttga tttaataaat   420
gaaagtaaaa ctgagtctaa attatcaaaa acatttaatt atacaacttc taaaacagtt   480
```

-continued

```
tctaaaacag ataactttaa atttggagaa aaaataggag taaaaacatc atttaaagta      540
ggtcttgaag ctatagctga cagtaaagtt gagacaagct ttgaatttaa tgcagaacaa      600
ggttggtcaa atacaaatag tactactgaa actaaacaag aaagtactac atatactgca      660
acagtttctc cacaaactaa aaagagatta ttcctagatg tgttaggatc acaaattgat      720
attccttatg aaggaaaaat atatatggaa tacgacatag aattaatggg atttttaaga      780
tatacaggaa atgctcgtga agatcatact gaagatagac caacagttaa acttaaattt      840
ggtaaaaacg gtatgagtgc tgaggaacat cttaaagatt tatatagtca taagaatatt      900
aatggatatt cagaatggga ttggaaatgg gtagatgaga aatttggtta tttatttaaa      960
aattcatacg atgctcttac tagtagaaaa ttaggaggaa taataaaagg ctcatttact     1020
aacattaatg gaacaaaaat agtaattaga gaaggtaaaa aaattccact tcctgataag     1080
aagagaagag gaaaacgttc agtagattct ttagatgcta gattacaaaa tgaaggtatt     1140
agaatagaaa atattgaaac acaagatgtt ccaggattta gactaaatag cataacatac     1200
aatgataaaa aattgatatt aattaataat ata                                  1233
```

<210> SEQ ID NO 3
<211> LENGTH: 411
<212> TYPE: PRT
<213> ORGANISM: Artificial sequence
<220> FEATURE:
<223> OTHER INFORMATION: Completely synthesized.
<220> FEATURE:
<221> NAME/KEY: MISC_FEATURE
<222> LOCATION: (53)..(53)
<223> OTHER INFORMATION: Xaa at position 53 is ala, cys, asp, glu, phe,
    gly, his, ile, lys , leu, met, asn, pro, gln, arg, ser, thr, val,
    trp, or tyr.
<220> FEATURE:
<221> NAME/KEY: MISC_FEATURE
<222> LOCATION: (54)..(54)
<223> OTHER INFORMATION: Xaa at position 54 is ala, cys, asp, glu, phe,
    gly, his, ile, lys , leu, met, asn, pro, gln, arg, ser, thr, val,
    trp, or tyr.
<220> FEATURE:
<221> NAME/KEY: MISC_FEATURE
<222> LOCATION: (62)..(62)
<223> OTHER INFORMATION: Xaa at position 62 is ala, cys, asp, glu, phe,
    gly, his, ile, lys , leu, met, asn, pro, gln, arg, ser, thr, val,
    trp, or tyr.
<220> FEATURE:
<221> NAME/KEY: MISC_FEATURE
<222> LOCATION: (84)..(84)
<223> OTHER INFORMATION: Xaa at position 84 is ala, cys, asp, glu, phe,
    gly, his, ile, lys , leu, met, asn, pro, gln, arg, ser, thr, val,
    trp, or tyr.
<220> FEATURE:
<221> NAME/KEY: MISC_FEATURE
<222> LOCATION: (85)..(85)
<223> OTHER INFORMATION: Xaa at position 85 is ala, cys, asp, glu, phe,
    gly, his, ile, lys , leu, met, asn, pro, gln, arg, ser, thr, val,
    trp, or tyr.
<220> FEATURE:
<221> NAME/KEY: MISC_FEATURE
<222> LOCATION: (86)..(86)
<223> OTHER INFORMATION: Xaa at position 86 is ala, cys, asp, glu, phe,
    gly, his, ile, lys , leu, met, asn, pro, gln, arg, ser, thr, val,
    trp, or tyr.
<220> FEATURE:
<221> NAME/KEY: MISC_FEATURE
<222> LOCATION: (87)..(87)
<223> OTHER INFORMATION: Xaa at position 87 is ala, cys, asp, glu, phe,
    gly, his, ile, lys , leu, met, asn, pro, gln, arg, ser, thr, val,
    trp, or tyr.
<220> FEATURE:
<221> NAME/KEY: MISC_FEATURE
<222> LOCATION: (88)..(88)
<223> OTHER INFORMATION: Xaa at position 88 is ala, cys, asp, glu, phe,

```
        gly, his, ile, lys , leu, met, asn, pro, gln, arg, ser, thr, val,
        trp, or tyr.
<220> FEATURE:
<221> NAME/KEY: MISC_FEATURE
<222> LOCATION: (89)..(89)
<223> OTHER INFORMATION: Xaa at position 89 is ala, cys, asp, glu, phe,
        gly, his, ile, lys , leu, met, asn, pro, gln, arg, ser, thr, val,
        trp, or tyr.
<220> FEATURE:
<221> NAME/KEY: MISC_FEATURE
<222> LOCATION: (90)..(90)
<223> OTHER INFORMATION: Xaa at position 90 is ala, cys, asp, glu, phe,
        gly, his, ile, lys , leu, met, asn, pro, gln, arg, ser, thr, val,
        trp, or tyr.
<220> FEATURE:
<221> NAME/KEY: MISC_FEATURE
<222> LOCATION: (91)..(91)
<223> OTHER INFORMATION: Xaa at position 91 is ala, cys, asp, glu, phe,
        gly, his, ile, lys , leu, met, asn, pro, gln, arg, ser, thr, val,
        trp, or tyr.
<220> FEATURE:
<221> NAME/KEY: MISC_FEATURE
<222> LOCATION: (92)..(92)
<223> OTHER INFORMATION: Xaa at position 92 is ala, cys, asp, glu, phe,
        gly, his, ile, lys , leu, met, asn, pro, gln, arg, ser, thr, val,
        trp, or tyr.
<220> FEATURE:
<221> NAME/KEY: MISC_FEATURE
<222> LOCATION: (93)..(93)
<223> OTHER INFORMATION: Xaa at position 93 is ala, cys, asp, glu, phe,
        gly, his, ile, lys , leu, met, asn, pro, gln, arg, ser, thr, val,
        trp, or tyr.
<220> FEATURE:
<221> NAME/KEY: MISC_FEATURE
<222> LOCATION: (94)..(94)
<223> OTHER INFORMATION: Xaa at position 94 is ala, cys, asp, glu, phe,
        gly, his, ile, lys , leu, met, asn, pro, gln, arg, ser, thr, val,
        trp, or tyr.
<220> FEATURE:
<221> NAME/KEY: MISC_FEATURE
<222> LOCATION: (95)..(95)
<223> OTHER INFORMATION: Xaa at position 95 is ala, cys, asp, glu, phe,
        gly, his, ile, lys , leu, met, asn, pro, gln, arg, ser, thr, val,
        trp, or tyr.
<220> FEATURE:
<221> NAME/KEY: MISC_FEATURE
<222> LOCATION: (96)..(96)
<223> OTHER INFORMATION: Xaa at position 96 is ala, cys, asp, glu, phe,
        gly, his, ile, lys , leu, met, asn, pro, gln, arg, ser, thr, val,
        trp, or tyr.
<220> FEATURE:
<221> NAME/KEY: MISC_FEATURE
<222> LOCATION: (97)..(97)
<223> OTHER INFORMATION: Xaa at position 97 is ala, cys, asp, glu, phe,
        gly, his, ile, lys , leu, met, asn, pro, gln, arg, ser, thr, val,
        trp, or tyr.
<220> FEATURE:
<221> NAME/KEY: MISC_FEATURE
<222> LOCATION: (98)..(98)
<223> OTHER INFORMATION: Xaa at position 98 is ala, cys, asp, glu, phe,
        gly, his, ile, lys , leu, met, asn, pro, gln, arg, ser, thr, val,
        trp, or tyr.
<220> FEATURE:
<221> NAME/KEY: MISC_FEATURE
<222> LOCATION: (99)..(99)
<223> OTHER INFORMATION: Xaa at position 99 is ala, cys, asp, glu, phe,
        gly, his, ile, lys , leu, met, asn, pro, gln, arg, ser, thr, val,
        trp, or tyr.
<220> FEATURE:
<221> NAME/KEY: MISC_FEATURE
<222> LOCATION: (100)..(100)
<223> OTHER INFORMATION: Xaa at position 100 is ala, cys, asp, glu, phe,
        gly, his, ile, lys, leu, met, asn, pro, gln, arg, ser, thr, val,
        trp, or tyr.
<220> FEATURE:
<221> NAME/KEY: MISC_FEATURE
<222> LOCATION: (101)..(101)
<223> OTHER INFORMATION: Xaa at position 101 is ala, cys, asp, glu, phe,
        gly, his, ile, lys, leu, met, asn, pro, gln, arg, ser, thr, val,
```

```
            trp, or tyr.
<220> FEATURE:
<221> NAME/KEY: MISC_FEATURE
<222> LOCATION: (102)..(102)
<223> OTHER INFORMATION: Xaa at position 102 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
<222> LOCATION: (168)..(168)
<223> OTHER INFORMATION: Xaa at position 168 is asp, glu, phe, his, lys,
      or arg.
<220> FEATURE:
<221> NAME/KEY: MISC_FEATURE
<222> LOCATION: (170)..(170)
<223> OTHER INFORMATION: Xaa at position 170 is asp, glu, his, lys, or
      arg.
<220> FEATURE:
<221> NAME/KEY: MISC_FEATURE
<222> LOCATION: (172)..(172)
<223> OTHER INFORMATION: Xaa at position 172 is asp, glu, his, ile, lys,
      or arg.
<220> FEATURE:
<221> NAME/KEY: MISC_FEATURE
<222> LOCATION: (174)..(174)
<223> OTHER INFORMATION: Xaa at position 174 is asp, glu, his, lys, arg,
      or val.
<220> FEATURE:
<221> NAME/KEY: MISC_FEATURE
<222> LOCATION: (176)..(176)
<223> OTHER INFORMATION: Xaa at position 176 is asp, glu, his, lys, arg,
      or thr.
<220> FEATURE:
<221> NAME/KEY: MISC_FEATURE
<222> LOCATION: (178)..(178)
<223> OTHER INFORMATION: Xaa at position 178 is asp, glu, phe, his, lys,
      or arg.
<220> FEATURE:
<221> NAME/KEY: MISC_FEATURE
<222> LOCATION: (180)..(180)
<223> OTHER INFORMATION: Xaa at position 180 is asp, glu, his, lys, arg,
      or val.
<220> FEATURE:
<221> NAME/KEY: MISC_FEATURE
<222> LOCATION: (182)..(182)
<223> OTHER INFORMATION: Xaa at position 182 is asp, glu, his, lys, arg,
      or leu.
<220> FEATURE:
<221> NAME/KEY: MISC_FEATURE
<222> LOCATION: (184)..(184)
<223> OTHER INFORMATION: Xaa at position 184 is ala, asp, glu, his, lys,
      or arg.
<220> FEATURE:
<221> NAME/KEY: MISC_FEATURE
<222> LOCATION: (186)..(186)
<223> OTHER INFORMATION: Xaa at position 186 is ala, asp, glu, his, lys,
      or arg.
<220> FEATURE:
<221> NAME/KEY: MISC_FEATURE
<222> LOCATION: (188)..(188)
<223> OTHER INFORMATION: Xaa at position 188 is asp, glu, his, lys, arg,
      or ser.
<220> FEATURE:
<221> NAME/KEY: MISC_FEATURE
<222> LOCATION: (190)..(190)
<223> OTHER INFORMATION: Xaa at position 190 is asp, glu, his, lys, arg,
      or val.
<220> FEATURE:
<221> NAME/KEY: MISC_FEATURE
<222> LOCATION: (192)..(192)
<223> OTHER INFORMATION: Xaa at position 192 is asp, glu, his, lys, arg,
      or thr.
<220> FEATURE:
<221> NAME/KEY: MISC_FEATURE
<222> LOCATION: (194)..(194)
<223> OTHER INFORMATION: Xaa at position 194 is asp, glu, phe, his, lys,
      or arg.
<220> FEATURE:
<221> NAME/KEY: MISC_FEATURE
```

```
<222> LOCATION: (196)..(196)
<223> OTHER INFORMATION: Xaa at position 196 is asp, glu, phe, his, lys,
      or arg.
<220> FEATURE:
<221> NAME/KEY: MISC_FEATURE
<222> LOCATION: (198)..(198)
<223> OTHER INFORMATION: Xaa at position 198 is ala, asp, glu, his, lys,
      or arg.
<220> FEATURE:
<221> NAME/KEY: MISC_FEATURE
<222> LOCATION: (200)..(200)
<223> OTHER INFORMATION: Xaa at position 200 is asp, glu, his, lys, gln,
      or arg.
<220> FEATURE:
<221> NAME/KEY: MISC_FEATURE
<222> LOCATION: (202)..(202)
<223> OTHER INFORMATION: Xaa at position 202 is asp, glu, his, lys, arg,
      or trp.
<220> FEATURE:
<221> NAME/KEY: MISC_FEATURE
<222> LOCATION: (204)..(204)
<223> OTHER INFORMATION: Xaa at position 204 is asp, glu, his, lys, asn,
      or arg.
<220> FEATURE:
<221> NAME/KEY: MISC_FEATURE
<222> LOCATION: (259)..(259)
<223> OTHER INFORMATION: Xaa at position 259 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
<222> LOCATION: (260)..(260)
<223> OTHER INFORMATION: Xaa at position 260 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
<222> LOCATION: (261)..(261)
<223> OTHER INFORMATION: Xaa at position 261 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
<222> LOCATION: (262)..(262)
<223> OTHER INFORMATION: Xaa at position 262 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
<222> LOCATION: (263)..(263)
<223> OTHER INFORMATION: Xaa at position 263 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
<222> LOCATION: (264)..(264)
<223> OTHER INFORMATION: Xaa at position 264 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
<222> LOCATION: (265)..(265)
<223> OTHER INFORMATION: Xaa at position 265 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
<222> LOCATION: (266)..(266)
<223> OTHER INFORMATION: Xaa at position 266 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
<222> LOCATION: (267)..(267)
<223> OTHER INFORMATION: Xaa at position 267 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
```

-continued

```
<222> LOCATION: (268)..(268)
<223> OTHER INFORMATION: Xaa at position 268 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
<222> LOCATION: (269)..(269)

<223> OTHER INFORMATION: Xaa at position 269 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
<222> LOCATION: (270)..(270)
<223> OTHER INFORMATION: Xaa at position 270 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
<222> LOCATION: (271)..(271)
<223> OTHER INFORMATION: Xaa at position 271 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
<222> LOCATION: (272)..(272)
<223> OTHER INFORMATION: Xaa at position 272 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
<222> LOCATION: (273)..(273)
<223> OTHER INFORMATION: Xaa at position 273 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
<222> LOCATION: (274)..(274)
<223> OTHER INFORMATION: Xaa at position 274 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
<222> LOCATION: (309)..(309)
<223> OTHER INFORMATION: Xaa at position 309 is ala, cys, asp, glu,
      phe, gly, his, ile, lys, leu, met, asn, pro, gln, arg, ser, thr,
      val, trp, or tyr.
<220> FEATURE:
<221> NAME/KEY: MISC_FEATURE
<222> LOCATION: (310)..(310)
<223> OTHER INFORMATION: Xaa at position 310 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
<222> LOCATION: (311)..(311)
<223> OTHER INFORMATION: Xaa at position 311 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
<222> LOCATION: (312)..(312)
<223> OTHER INFORMATION: Xaa at position 312 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
<222> LOCATION: (313)..(313)
<223> OTHER INFORMATION: Xaa at position 313 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
<222> LOCATION: (314)..(314)
<223> OTHER INFORMATION: Xaa at position 314 is ala, cys, asp, glu, phe,
      gly, his, ile, lys, leu, met, asn, pro, gln, arg, ser, thr, val,
      trp, or tyr.
<220> FEATURE:
<221> NAME/KEY: MISC_FEATURE
```

<222> LOCATION: (315)..(315)
<223> OTHER INFORMATION: Xaa at position 315 is ala, cys, asp, glu, phe, gly, his, ile, lys, leu, met, asn, pro, gln, arg, ser, thr, val, trp, or tyr.

<400> SEQUENCE: 3

```
Thr Asn Leu Glu Glu Gly Gly Tyr Ala Asn His Asn Asn Ala Ser Ser
1               5                   10                  15

Ile Lys Ile Phe Gly Tyr Glu Asp Asn Glu Asp Leu Lys Ala Lys Ile
            20                  25                  30

Ile Gln Asp Pro Glu Phe Ile Arg Asn Trp Ala Asn Val Ala His Ser
        35                  40                  45

Leu Gly Phe Gly Xaa Xaa Gly Gly Thr Ala Asn Pro Asn Xaa Gly Gln
    50                  55                  60

Gly Phe Glu Phe Lys Arg Glu Val Gly Ala Gly Lys Val Ser Tyr
65                  70                  75                  80

Leu Leu Ser Xaa Xaa Xaa Xaa Xaa Xaa Xaa Xaa Xaa Xaa Xaa Xaa
                85                  90                  95

Xaa Xaa Xaa Xaa Xaa Xaa Ser Met Lys Ile Ser Asn Val Arg Phe Val
            100                 105                 110

Ile Asp Asn Asp Ser Ile Lys Leu Gly Thr Pro Lys Val Lys Lys Leu
            115                 120                 125

Ala Pro Leu Asn Ser Ala Ser Phe Asp Leu Ile Asn Glu Ser Lys Thr
130                 135                 140

Glu Ser Lys Leu Ser Lys Thr Phe Asn Tyr Thr Thr Ser Lys Thr Val
145                 150                 155                 160

Ser Lys Thr Asp Asn Phe Lys Xaa Gly Xaa Lys Xaa Gly Xaa Lys Xaa
            165                 170                 175

Ser Xaa Lys Xaa Gly Xaa Glu Xaa Ile Xaa Asp Xaa Lys Xaa Glu Xaa
        180                 185                 190

Ser Xaa Glu Xaa Asn Xaa Glu Xaa Gly Xaa Ser Xaa Thr Asn Ser Thr
        195                 200                 205

Thr Glu Thr Lys Gln Glu Ser Thr Thr Tyr Thr Ala Thr Val Ser Pro
210                 215                 220

Gln Thr Lys Lys Arg Leu Phe Leu Asp Val Leu Gly Ser Gln Ile Asp
225                 230                 235                 240

Ile Pro Tyr Glu Gly Lys Ile Tyr Met Glu Tyr Asp Ile Glu Leu Met
            245                 250                 255

Gly Phe Xaa Xaa Xaa Xaa Xaa Xaa Xaa Xaa Xaa Xaa Xaa Xaa Xaa
            260                 265                 270

Xaa Xaa Thr Val Lys Leu Lys Phe Gly Lys Asn Gly Met Ser Ala Glu
        275                 280                 285

Glu His Leu Lys Asp Leu Tyr Ser His Lys Asn Ile Asn Gly Tyr Ser
290                 295                 300

Glu Trp Asp Trp Xaa Xaa Xaa Xaa Xaa Xaa Gly Tyr Leu Phe Lys
305                 310                 315                 320

Asn Ser Tyr Asp Ala Leu Thr Ser Arg Lys Leu Gly Ile Ile Lys
            325                 330                 335

Gly Ser Phe Thr Asn Ile Asn Gly Thr Lys Ile Val Ile Arg Glu Gly
            340                 345                 350

Lys Glu Ile Pro Leu Pro Asp Lys Lys Arg Gly Lys Arg Ser Val
        355                 360                 365

Asp Ser Leu Asp Ala Arg Leu Gln Asn Glu Gly Ile Arg Ile Glu Asn
370                 375                 380
```

```
Ile Glu Thr Gln Asp Val Pro Gly Phe Arg Leu Asn Ser Ile Thr Tyr
385                 390                 395                 400

Asn Asp Lys Lys Leu Ile Leu Ile Asn Asn Ile
            405                 410

<210> SEQ ID NO 4
<211> LENGTH: 411
<212> TYPE: PRT
<213> ORGANISM: Clostridium septicum
<220> FEATURE:
<221> NAME/KEY: MISC_FEATURE
<222> LOCATION: (54)..(54)
<223> OTHER INFORMATION: Xaa at position 54 is ala, cys, asp, glu, phe,
      gly, his, ile, lys , leu, met, asn, pro, gln, arg, ser, thr, val,
      trp, or tyr.
<220> FEATURE:
<221> NAME/KEY: MISC_FEATURE
<222> LOCATION: (54)..(54)
<223> OTHER INFORMATION: Xaa at position 54 is ala, cys, asp, glu, phe,
      gly, his, ile,lys,leu, met, asn, pro, gln, arg, ser, thr, val,
      trp, or tyr.

<400> SEQUENCE: 4

Thr Asn Leu Glu Glu Gly Gly Tyr Ala Asn His Asn Asn Ala Ser Ser
1               5                   10                  15

Ile Lys Ile Phe Gly Tyr Glu Asp Asn Glu Asp Leu Lys Ala Lys Ile
            20                  25                  30

Ile Gln Asp Pro Glu Phe Ile Arg Asn Trp Ala Asn Val Ala His Ser
        35                  40                  45

Leu Gly Phe Gly Trp Xaa Gly Gly Thr Ala Asn Pro Asn Val Gly Gln
    50                  55                  60

Gly Phe Glu Phe Lys Arg Glu Val Gly Ala Gly Lys Val Ser Tyr
65                  70                  75                  80

Leu Leu Ser Ala Arg Tyr Asn Pro Asn Asp Pro Tyr Ala Ser Gly Tyr
                85                  90                  95

Arg Ala Lys Asp Arg Leu Ser Met Lys Ile Ser Asn Val Arg Phe Val
            100                 105                 110

Ile Asp Asn Asp Ser Ile Lys Leu Gly Thr Pro Lys Val Lys Lys Leu
        115                 120                 125

Ala Pro Leu Asn Ser Ala Ser Phe Asp Leu Ile Asn Glu Ser Lys Thr
    130                 135                 140

Glu Ser Lys Leu Ser Lys Thr Phe Asn Tyr Thr Thr Ser Lys Thr Val
145                 150                 155                 160

Ser Lys Thr Asp Asn Phe Lys Phe Gly Glu Lys Ile Gly Val Lys Thr
                165                 170                 175

Ser Phe Lys Val Gly Leu Glu Ala Ile Ala Asp Ser Lys Val Glu Thr
            180                 185                 190

Ser Phe Glu Phe Asn Ala Glu Gln Gly Trp Ser Asn Thr Asn Ser Thr
        195                 200                 205

Thr Glu Thr Lys Gln Glu Ser Thr Thr Tyr Thr Ala Thr Val Ser Pro
    210                 215                 220

Gln Thr Lys Lys Arg Leu Phe Leu Asp Val Leu Gly Ser Gln Ile Asp
225                 230                 235                 240

Ile Pro Tyr Glu Gly Lys Ile Tyr Met Glu Tyr Asp Ile Glu Leu Met
                245                 250                 255

Gly Phe Leu Arg Tyr Thr Gly Asn Ala Arg Glu Asp His Thr Glu Asp
            260                 265                 270

Arg Pro Thr Val Lys Leu Lys Phe Gly Lys Asn Gly Met Ser Ala Glu
        275                 280                 285
```

```
Glu His Leu Lys Asp Leu Tyr Ser His Lys Asn Ile Asn Gly Tyr Ser
        290                 295                 300

Glu Trp Asp Trp Lys Trp Val Asp Glu Lys Phe Gly Tyr Leu Phe Lys
305                 310                 315                 320

Asn Ser Tyr Asp Ala Leu Thr Ser Arg Lys Leu Gly Ile Ile Lys
                325                 330                 335

Gly Ser Phe Thr Asn Ile Asn Gly Thr Lys Ile Val Ile Arg Glu Gly
                340                 345                 350

Lys Glu Ile Pro Leu Pro Asp Lys Lys Arg Gly Lys Arg Ser Val
                355                 360                 365

Asp Ser Leu Asp Ala Arg Leu Gln Asn Glu Gly Ile Arg Ile Glu Asn
        370                 375                 380

Ile Glu Thr Gln Asp Val Pro Gly Phe Arg Leu Asn Ser Ile Thr Tyr
385                 390                 395                 400

Asn Asp Lys Lys Leu Ile Leu Ile Asn Asn Ile
                405                 410

<210> SEQ ID NO 5
<211> LENGTH: 411
<212> TYPE: PRT
<213> ORGANISM: Artificial sequence
<220> FEATURE:
<223> OTHER INFORMATION: Completely synthesized.
<220> FEATURE:
<221> NAME/KEY: MISC_FEATURE
<222> LOCATION: (62)..(62)
<223> OTHER INFORMATION: Xaa at position 62 is ala, cys, asp, glu, phe,
      gly, his, ile, lys , leu, met, asn, pro, gln, arg, ser, thr, val,
      trp, or tyr.

<400> SEQUENCE: 5

Thr Asn Leu Glu Glu Gly Gly Tyr Ala Asn His Asn Asn Ala Ser Ser
1               5                   10                  15

Ile Lys Ile Phe Gly Tyr Glu Asp Asn Glu Asp Leu Lys Ala Lys Ile
                20                  25                  30

Ile Gln Asp Pro Glu Phe Ile Arg Asn Trp Ala Asn Val Ala His Ser
        35                  40                  45

Leu Gly Phe Gly Trp Cys Gly Gly Thr Ala Asn Pro Asn Xaa Gly Gln
50                  55                  60

Gly Phe Glu Phe Lys Arg Glu Val Gly Ala Gly Lys Val Ser Tyr
65                  70                  75                  80

Leu Leu Ser Ala Arg Tyr Asn Pro Asn Asp Pro Tyr Ala Ser Gly Tyr
                85                  90                  95

Arg Ala Lys Asp Arg Leu Ser Met Lys Ile Ser Asn Val Arg Phe Val
                100                 105                 110

Ile Asp Asn Asp Ser Ile Lys Leu Gly Thr Pro Lys Val Lys Lys Leu
        115                 120                 125

Ala Pro Leu Asn Ser Ala Ser Phe Asp Leu Ile Asn Glu Ser Lys Thr
        130                 135                 140

Glu Ser Lys Leu Ser Lys Thr Phe Asn Tyr Thr Thr Ser Lys Thr Val
145                 150                 155                 160

Ser Lys Thr Asp Asn Phe Lys Phe Gly Glu Lys Ile Gly Val Lys Thr
                165                 170                 175

Ser Phe Lys Val Gly Leu Glu Ala Ile Ala Asp Ser Lys Val Glu Thr
                180                 185                 190

Ser Phe Glu Phe Asn Ala Glu Gln Gly Trp Ser Asn Thr Asn Ser Thr
                195                 200                 205
```

-continued

```
Thr Glu Thr Lys Gln Glu Ser Thr Thr Tyr Thr Ala Thr Val Ser Pro
    210                 215                 220
Gln Thr Lys Lys Arg Leu Phe Leu Asp Val Leu Gly Ser Gln Ile Asp
225                 230                 235                 240
Ile Pro Tyr Glu Gly Lys Ile Tyr Met Glu Tyr Asp Ile Glu Leu Met
                245                 250                 255
Gly Phe Leu Arg Tyr Thr Gly Asn Ala Arg Glu Asp His Thr Glu Asp
            260                 265                 270
Arg Pro Thr Val Lys Leu Lys Phe Gly Lys Asn Gly Met Ser Ala Glu
        275                 280                 285
Glu His Leu Lys Asp Leu Tyr Ser His Lys Asn Ile Asn Gly Tyr Ser
    290                 295                 300
Glu Trp Asp Trp Lys Trp Val Asp Glu Lys Phe Gly Tyr Leu Phe Lys
305                 310                 315                 320
Asn Ser Tyr Asp Ala Leu Thr Ser Arg Lys Leu Gly Gly Ile Ile Lys
                325                 330                 335
Gly Ser Phe Thr Asn Ile Asn Gly Thr Lys Ile Val Ile Arg Glu Gly
            340                 345                 350
Lys Glu Ile Pro Leu Pro Asp Lys Lys Arg Arg Gly Lys Arg Ser Val
        355                 360                 365
Asp Ser Leu Asp Ala Arg Leu Gln Asn Glu Gly Ile Arg Ile Glu Asn
    370                 375                 380
Ile Glu Thr Gln Asp Val Pro Gly Phe Arg Leu Asn Ser Ile Thr Tyr
385                 390                 395                 400
Asn Asp Lys Lys Leu Ile Leu Ile Asn Asn Ile
                405                 410
```

<210> SEQ ID NO 6
<211> LENGTH: 411
<212> TYPE: PRT
<213> ORGANISM: Artificial sequence
<220> FEATURE:
<223> OTHER INFORMATION: Completely synthesized.
<220> FEATURE:
<221> NAME/KEY: MISC_FEATURE
<222> LOCATION: (90)..(90)
<223> OTHER INFORMATION: Xaa at position 90 is ala, cys, asp, glu, phe,
    gly, his, ile, lys , leu, met, asn, pro, gln, arg, ser, thr, val,
    trp, or tyr.

<400> SEQUENCE: 6

```
Thr Asn Leu Glu Glu Gly Gly Tyr Ala Asn His Asn Asn Ala Ser Ser
1               5                   10                  15
Ile Lys Ile Phe Gly Tyr Glu Asp Asn Glu Asp Leu Lys Ala Lys Ile
                20                  25                  30
Ile Gln Asp Pro Glu Phe Ile Arg Asn Trp Ala Asn Val Ala His Ser
            35                  40                  45
Leu Gly Phe Gly Trp Cys Gly Gly Thr Ala Asn Pro Asn Val Gly Gln
        50                  55                  60
Gly Phe Glu Phe Lys Arg Glu Val Gly Ala Gly Lys Val Ser Tyr
65                  70                  75                  80
Leu Leu Ser Ala Arg Tyr Asn Pro Asn Xaa Pro Tyr Ala Ser Gly Tyr
                85                  90                  95
Arg Ala Lys Asp Arg Leu Ser Met Lys Ile Ser Asn Val Arg Phe Val
            100                 105                 110
Ile Asp Asn Asp Ser Ile Lys Leu Gly Thr Pro Lys Val Lys Lys Leu
        115                 120                 125
```

```
Ala Pro Leu Asn Ser Ala Ser Phe Asp Leu Ile Asn Glu Ser Lys Thr
        130                 135                 140

Glu Ser Lys Leu Ser Lys Thr Phe Asn Tyr Thr Thr Ser Lys Thr Val
145                 150                 155                 160

Ser Lys Thr Asp Asn Phe Lys Phe Gly Glu Lys Ile Gly Val Lys Thr
                165                 170                 175

Ser Phe Lys Val Gly Leu Glu Ala Ile Ala Asp Ser Lys Val Glu Thr
            180                 185                 190

Ser Phe Glu Phe Asn Ala Glu Gln Gly Trp Ser Asn Thr Asn Ser Thr
        195                 200                 205

Thr Glu Thr Lys Gln Glu Ser Thr Thr Tyr Thr Ala Thr Val Ser Pro
    210                 215                 220

Gln Thr Lys Lys Arg Leu Phe Leu Asp Val Leu Gly Ser Gln Ile Asp
225                 230                 235                 240

Ile Pro Tyr Glu Gly Lys Ile Tyr Met Glu Tyr Asp Ile Glu Leu Met
                245                 250                 255

Gly Phe Leu Arg Tyr Thr Gly Asn Ala Arg Glu Asp His Thr Glu Asp
            260                 265                 270

Arg Pro Thr Val Lys Leu Lys Phe Gly Lys Asn Gly Met Ser Ala Glu
        275                 280                 285

Glu His Leu Lys Asp Leu Tyr Ser His Lys Asn Ile Asn Gly Tyr Ser
    290                 295                 300

Glu Trp Asp Trp Lys Trp Val Asp Glu Lys Phe Gly Tyr Leu Phe Lys
305                 310                 315                 320

Asn Ser Tyr Asp Ala Leu Thr Ser Arg Lys Leu Gly Ile Ile Lys
                325                 330                 335

Gly Ser Phe Thr Asn Ile Asn Gly Thr Lys Ile Val Ile Arg Glu Gly
            340                 345                 350

Lys Glu Ile Pro Leu Pro Asp Lys Lys Arg Arg Gly Lys Arg Ser Val
        355                 360                 365

Asp Ser Leu Asp Ala Arg Leu Gln Asn Glu Gly Ile Arg Ile Glu Asn
    370                 375                 380

Ile Glu Thr Gln Asp Val Pro Gly Phe Arg Leu Asn Ser Ile Thr Tyr
385                 390                 395                 400

Asn Asp Lys Lys Leu Ile Leu Ile Asn Asn Ile
                405                 410

<210> SEQ ID NO 7
<211> LENGTH: 411
<212> TYPE: PRT
<213> ORGANISM: Artificial sequence
<220> FEATURE:
<223> OTHER INFORMATION: Completely synthesized.
<220> FEATURE:
<221> NAME/KEY: MISC_FEATURE
<222> LOCATION: (92)..(92)
<223> OTHER INFORMATION: Xaa at position 92 is ala, cys, asp, glu, phe,
      gly, his, ile, lys , leu, met, asn, pro, gln, arg, ser, thr, val,
      trp, or tyr.

<400> SEQUENCE: 7

Thr Asn Leu Glu Glu Gly Gly Tyr Ala Asn His Asn Asn Ala Ser Ser
1               5                   10                  15

Ile Lys Ile Phe Gly Tyr Glu Asp Asn Glu Asp Leu Lys Ala Lys Ile
            20                  25                  30

Ile Gln Asp Pro Glu Phe Ile Arg Asn Trp Ala Asn Val Ala His Ser
        35                  40                  45
```

```
Leu Gly Phe Gly Trp Cys Gly Gly Thr Ala Asn Pro Asn Val Gly Gln
         50                  55                  60

Gly Phe Glu Phe Lys Arg Glu Val Gly Ala Gly Lys Val Ser Tyr
 65                  70                  75                  80

Leu Leu Ser Ala Arg Tyr Asn Pro Asn Asp Pro Xaa Ala Ser Gly Tyr
                 85                  90                  95

Arg Ala Lys Asp Arg Leu Ser Met Lys Ile Ser Asn Val Arg Phe Val
            100                 105                 110

Ile Asp Asn Asp Ser Ile Lys Leu Gly Thr Pro Lys Val Lys Lys Leu
            115                 120                 125

Ala Pro Leu Asn Ser Ala Ser Phe Asp Leu Ile Asn Glu Ser Lys Thr
130                 135                 140

Glu Ser Lys Leu Ser Lys Thr Phe Asn Tyr Thr Thr Ser Lys Thr Val
145                 150                 155                 160

Ser Lys Thr Asp Asn Phe Lys Phe Gly Glu Lys Ile Gly Val Lys Thr
                165                 170                 175

Ser Phe Lys Val Gly Leu Glu Ala Ile Ala Asp Ser Lys Val Glu Thr
            180                 185                 190

Ser Phe Glu Phe Asn Ala Glu Gln Gly Trp Ser Asn Thr Asn Ser Thr
            195                 200                 205

Thr Glu Thr Lys Gln Glu Ser Thr Thr Tyr Thr Ala Thr Val Ser Pro
    210                 215                 220

Gln Thr Lys Lys Arg Leu Phe Leu Asp Val Leu Gly Ser Gln Ile Asp
225                 230                 235                 240

Ile Pro Tyr Glu Gly Lys Ile Tyr Met Glu Tyr Asp Ile Glu Leu Met
                245                 250                 255

Gly Phe Leu Arg Tyr Thr Gly Asn Ala Arg Glu Asp His Thr Glu Asp
            260                 265                 270

Arg Pro Thr Val Lys Leu Lys Phe Gly Lys Asn Gly Met Ser Ala Glu
        275                 280                 285

Glu His Leu Lys Asp Leu Tyr Ser His Lys Asn Ile Asn Gly Tyr Ser
290                 295                 300

Glu Trp Asp Trp Lys Trp Val Asp Glu Lys Phe Gly Tyr Leu Phe Lys
305                 310                 315                 320

Asn Ser Tyr Asp Ala Leu Thr Ser Arg Lys Leu Gly Gly Ile Ile Lys
                325                 330                 335

Gly Ser Phe Thr Asn Ile Asn Gly Thr Lys Ile Val Ile Arg Glu Gly
            340                 345                 350

Lys Glu Ile Pro Leu Pro Asp Lys Lys Arg Gly Lys Arg Ser Val
    355                 360                 365

Asp Ser Leu Asp Ala Arg Leu Gln Asn Glu Gly Ile Arg Ile Glu Asn
370                 375                 380

Ile Glu Thr Gln Asp Val Pro Gly Phe Arg Leu Asn Ser Ile Thr Tyr
385                 390                 395                 400

Asn Asp Lys Lys Leu Ile Leu Ile Asn Asn Ile
                405                 410

<210> SEQ ID NO 8
<211> LENGTH: 411
<212> TYPE: PRT
<213> ORGANISM: Artificial sequence
<220> FEATURE:
<223> OTHER INFORMATION: Completely synthesized.
<220> FEATURE:
<221> NAME/KEY: MISC_FEATURE
```

<222> LOCATION: (96)..(96)
<223> OTHER INFORMATION: Xaa at position 96 is ala, cys, asp, glu, phe, gly, his, ile, lys , leu, met, asn, pro, gln, arg, ser, thr, val, trp, or tyr.

<400> SEQUENCE: 8

```
Thr Asn Leu Glu Glu Gly Gly Tyr Ala Asn His Asn Ala Ser Ser
1               5                   10                  15

Ile Lys Ile Phe Gly Tyr Glu Asp Asn Glu Asp Leu Lys Ala Lys Ile
            20                  25                  30

Ile Gln Asp Pro Glu Phe Ile Arg Asn Trp Ala Asn Val Ala His Ser
        35                  40                  45

Leu Gly Phe Gly Trp Cys Gly Gly Thr Ala Asn Pro Asn Val Gly Gln
    50                  55                  60

Gly Phe Glu Phe Lys Arg Glu Val Gly Ala Gly Lys Val Ser Tyr
65                  70                  75                  80

Leu Leu Ser Ala Arg Tyr Asn Pro Asn Asp Pro Tyr Ala Ser Gly Xaa
                85                  90                  95

Arg Ala Lys Asp Arg Leu Ser Met Lys Ile Ser Asn Val Arg Phe Val
            100                 105                 110

Ile Asp Asn Asp Ser Ile Lys Leu Gly Thr Pro Lys Val Lys Lys Leu
        115                 120                 125

Ala Pro Leu Asn Ser Ala Ser Phe Asp Leu Ile Asn Glu Ser Lys Thr
    130                 135                 140

Glu Ser Lys Leu Ser Lys Thr Phe Asn Tyr Thr Thr Ser Lys Thr Val
145                 150                 155                 160

Ser Lys Thr Asp Asn Phe Lys Phe Gly Glu Lys Ile Gly Val Lys Thr
                165                 170                 175

Ser Phe Lys Val Gly Leu Glu Ala Ile Ala Asp Ser Lys Val Glu Thr
            180                 185                 190

Ser Phe Glu Phe Asn Ala Glu Gln Gly Trp Ser Asn Thr Asn Ser Thr
        195                 200                 205

Thr Glu Thr Lys Gln Glu Ser Thr Thr Tyr Thr Ala Thr Val Ser Pro
    210                 215                 220

Gln Thr Lys Lys Arg Leu Phe Leu Asp Val Leu Gly Ser Gln Ile Asp
225                 230                 235                 240

Ile Pro Tyr Glu Gly Lys Ile Tyr Met Glu Tyr Asp Ile Glu Leu Met
                245                 250                 255

Gly Phe Leu Arg Tyr Thr Gly Asn Ala Arg Glu Asp His Thr Glu Asp
            260                 265                 270

Arg Pro Thr Val Lys Leu Lys Phe Gly Lys Asn Gly Met Ser Ala Glu
        275                 280                 285

Glu His Leu Lys Asp Leu Tyr Ser His Lys Asn Ile Asn Gly Tyr Ser
    290                 295                 300

Glu Trp Asp Trp Lys Trp Val Asp Glu Lys Phe Gly Tyr Leu Phe Lys
305                 310                 315                 320

Asn Ser Tyr Asp Ala Leu Thr Ser Arg Lys Leu Gly Ile Ile Lys
                325                 330                 335

Gly Ser Phe Thr Asn Ile Asn Gly Thr Lys Ile Val Ile Arg Glu Gly
            340                 345                 350

Lys Glu Ile Pro Leu Pro Asp Lys Lys Arg Gly Lys Arg Ser Val
        355                 360                 365

Asp Ser Leu Asp Ala Arg Leu Gln Asn Glu Gly Ile Arg Ile Glu Asn
    370                 375                 380
```

-continued

```
Ile Glu Thr Gln Asp Val Pro Gly Phe Arg Leu Asn Ser Ile Thr Tyr
385                 390                 395                 400

Asn Asp Lys Lys Leu Ile Leu Ile Asn Asn Ile
                405                 410
```

<210> SEQ ID NO 9
<211> LENGTH: 411
<212> TYPE: PRT
<213> ORGANISM: Artificial sequence
<220> FEATURE:
<223> OTHER INFORMATION: Completely synthesized.
<220> FEATURE:
<221> NAME/KEY: MISC_FEATURE
<222> LOCATION: (97)..(97)
<223> OTHER INFORMATION: Xaa at positin 97 is ala, cys, asp, glu, phe,
       gly, his, ile, lys,leu, met, asn, pro, gln, arg, ser, thr, val,
       trp, or tyr.

<400> SEQUENCE: 9

```
Thr Asn Leu Glu Glu Gly Gly Tyr Ala Asn His Asn Asn Ala Ser Ser
1               5                   10                  15

Ile Lys Ile Phe Gly Tyr Glu Asp Asn Glu Asp Leu Lys Ala Lys Ile
            20                  25                  30

Ile Gln Asp Pro Glu Phe Ile Arg Asn Trp Ala Asn Val Ala His Ser
        35                  40                  45

Leu Gly Phe Gly Trp Cys Gly Gly Thr Ala Asn Pro Asn Val Gly Gln
    50                  55                  60

Gly Phe Glu Phe Lys Arg Glu Val Gly Ala Gly Lys Val Ser Tyr
65                  70                  75                  80

Leu Leu Ser Ala Arg Tyr Asn Pro Asn Asp Pro Tyr Ala Ser Gly Tyr
                85                  90                  95

Xaa Ala Lys Asp Arg Leu Ser Met Lys Ile Ser Asn Val Arg Phe Val
                100                 105                 110

Ile Asp Asn Asp Ser Ile Lys Leu Gly Thr Pro Lys Val Lys Lys Leu
            115                 120                 125

Ala Pro Leu Asn Ser Ala Ser Phe Asp Leu Ile Asn Glu Ser Lys Thr
    130                 135                 140

Glu Ser Lys Leu Ser Lys Thr Phe Asn Tyr Thr Thr Ser Lys Thr Val
145                 150                 155                 160

Ser Lys Thr Asp Asn Phe Lys Phe Gly Glu Lys Ile Gly Val Lys Thr
                165                 170                 175

Ser Phe Lys Val Gly Leu Glu Ala Ile Ala Asp Ser Lys Val Glu Thr
            180                 185                 190

Ser Phe Glu Phe Asn Ala Glu Gln Gly Trp Ser Asn Thr Asn Ser Thr
        195                 200                 205

Thr Glu Thr Lys Gln Glu Ser Thr Thr Tyr Thr Ala Thr Val Ser Pro
    210                 215                 220

Gln Thr Lys Lys Arg Leu Phe Leu Asp Val Leu Gly Ser Gln Ile Asp
225                 230                 235                 240

Ile Pro Tyr Glu Gly Lys Ile Tyr Met Glu Tyr Asp Ile Glu Leu Met
                245                 250                 255

Gly Phe Leu Arg Tyr Thr Gly Asn Ala Arg Glu Asp His Thr Glu Asp
            260                 265                 270

Arg Pro Thr Val Lys Leu Lys Phe Gly Lys Asn Gly Met Ser Ala Glu
        275                 280                 285

Glu His Leu Lys Asp Leu Tyr Ser His Lys Asn Ile Asn Gly Tyr Ser
    290                 295                 300
```

-continued

```
Glu Trp Asp Trp Lys Trp Val Asp Glu Lys Phe Gly Tyr Leu Phe Lys
305                 310                 315                 320

Asn Ser Tyr Asp Ala Leu Thr Ser Arg Lys Leu Gly Ile Ile Lys
            325                 330                 335

Gly Ser Phe Thr Asn Ile Asn Gly Thr Lys Ile Val Ile Arg Glu Gly
            340                 345                 350

Lys Glu Ile Pro Leu Pro Asp Lys Lys Arg Arg Gly Lys Arg Ser Val
            355                 360                 365

Asp Ser Leu Asp Ala Arg Leu Gln Asn Glu Gly Ile Arg Ile Glu Asn
    370                 375                 380

Ile Glu Thr Gln Asp Val Pro Gly Phe Arg Leu Asn Ser Ile Thr Tyr
385                 390                 395                 400

Asn Asp Lys Lys Leu Ile Leu Ile Asn Asn Ile
            405                 410
```

<210> SEQ ID NO 10
<211> LENGTH: 411
<212> TYPE: PRT
<213> ORGANISM: Artificial sequence
<220> FEATURE:
<223> OTHER INFORMATION: Completely synthesized.
<220> FEATURE:
<221> NAME/KEY: MISC_FEATURE
<222> LOCATION: (101)..(101)
<223> OTHER INFORMATION: Xaa at position 101 is ala, cys, asp, glu, phe,
      gly, his, ile, lys, leu, met, asn, pro, gln, arg, ser, thr, val,
      trp, or tyr.

<400> SEQUENCE: 10

```
Thr Asn Leu Glu Glu Gly Gly Tyr Ala Asn His Asn Asn Ala Ser Ser
1               5                   10                  15

Ile Lys Ile Phe Gly Tyr Glu Asp Asn Glu Asp Leu Lys Ala Lys Ile
            20                  25                  30

Ile Gln Asp Pro Glu Phe Ile Arg Asn Trp Ala Asn Val Ala His Ser
        35                  40                  45

Leu Gly Phe Gly Trp Cys Gly Gly Thr Ala Asn Pro Asn Val Gly Gln
50                  55                  60

Gly Phe Glu Phe Lys Arg Glu Val Gly Ala Gly Lys Val Ser Tyr
65              70                  75                  80

Leu Leu Ser Ala Arg Tyr Asn Pro Asn Asp Pro Tyr Ala Ser Gly Tyr
                85                  90                  95

Arg Ala Lys Asp Xaa Leu Ser Met Lys Ile Ser Asn Val Arg Phe Val
            100                 105                 110

Ile Asp Asn Asp Ser Ile Lys Leu Gly Thr Pro Lys Val Lys Lys Leu
            115                 120                 125

Ala Pro Leu Asn Ser Ala Ser Phe Asp Leu Ile Asn Glu Ser Lys Thr
    130                 135                 140

Glu Ser Lys Leu Ser Lys Thr Phe Asn Tyr Thr Thr Ser Lys Thr Val
145                 150                 155                 160

Ser Lys Thr Asp Asn Phe Lys Phe Gly Glu Lys Ile Gly Val Lys Thr
            165                 170                 175

Ser Phe Lys Val Gly Leu Glu Ala Ile Ala Asp Ser Lys Val Glu Thr
            180                 185                 190

Ser Phe Glu Phe Asn Ala Glu Gln Gly Trp Ser Asn Thr Asn Ser Thr
        195                 200                 205

Thr Glu Thr Lys Gln Glu Ser Thr Thr Tyr Thr Ala Thr Val Ser Pro
210                 215                 220
```

-continued

```
Gln Thr Lys Lys Arg Leu Phe Leu Asp Val Leu Gly Ser Gln Ile Asp
225                 230                 235                 240

Ile Pro Tyr Glu Gly Lys Ile Tyr Met Glu Tyr Asp Ile Glu Leu Met
                245                 250                 255

Gly Phe Leu Arg Tyr Thr Gly Asn Ala Arg Glu Asp His Thr Glu Asp
                260                 265                 270

Arg Pro Thr Val Lys Leu Lys Phe Gly Lys Asn Gly Met Ser Ala Glu
                275                 280                 285

Glu His Leu Lys Asp Leu Tyr Ser His Lys Asn Ile Asn Gly Tyr Ser
        290                 295                 300

Glu Trp Asp Trp Lys Trp Val Asp Glu Lys Phe Gly Tyr Leu Phe Lys
305                 310                 315                 320

Asn Ser Tyr Asp Ala Leu Thr Ser Arg Lys Leu Gly Ile Ile Lys
                325                 330                 335

Gly Ser Phe Thr Asn Ile Asn Gly Thr Lys Ile Val Ile Arg Glu Gly
                340                 345                 350

Lys Glu Ile Pro Leu Pro Asp Lys Lys Arg Arg Gly Lys Arg Ser Val
                355                 360                 365

Asp Ser Leu Asp Ala Arg Leu Gln Asn Glu Gly Ile Arg Ile Glu Asn
        370                 375                 380

Ile Glu Thr Gln Asp Val Pro Gly Phe Arg Leu Asn Ser Ile Thr Tyr
385                 390                 395                 400

Asn Asp Lys Lys Leu Ile Leu Ile Asn Asn Ile
                405                 410
```

<210> SEQ ID NO 11
<211> LENGTH: 411
<212> TYPE: PRT
<213> ORGANISM: Artificial sequence
<220> FEATURE:
<223> OTHER INFORMATION: Completely synthesized.
<220> FEATURE:
<221> NAME/KEY: MISC_FEATURE
<222> LOCATION: (102)..(102)
<223> OTHER INFORMATION: Xaa at position 102 is ala, cys, asp, glu, phe,
      gly, his, ile, lys, leu, met, asn, pro, gln, arg, ser, thr, val,
      trp, or tyr.

<400> SEQUENCE: 11

```
Thr Asn Leu Glu Glu Gly Gly Tyr Ala Asn His Asn Asn Ala Ser Ser
1               5                   10                  15

Ile Lys Ile Phe Gly Tyr Glu Asp Asn Glu Asp Leu Lys Ala Lys Ile
                20                  25                  30

Ile Gln Asp Pro Glu Phe Ile Arg Asn Trp Ala Asn Val Ala His Ser
            35                  40                  45

Leu Gly Phe Gly Trp Cys Gly Gly Thr Ala Asn Pro Asn Val Gly Gln
    50                  55                  60

Gly Phe Glu Phe Lys Arg Glu Val Gly Ala Gly Gly Lys Val Ser Tyr
65              70                  75                  80

Leu Leu Ser Ala Arg Tyr Asn Pro Asn Asp Pro Tyr Ala Ser Gly Tyr
                85                  90                  95

Arg Ala Lys Asp Arg Xaa Ser Met Lys Ile Ser Asn Val Arg Phe Val
            100                 105                 110

Ile Asp Asn Asp Ser Ile Lys Leu Gly Thr Pro Lys Val Lys Lys Leu
        115                 120                 125

Ala Pro Leu Asn Ser Ala Ser Phe Asp Leu Ile Asn Glu Ser Lys Thr
    130                 135                 140
```

-continued

```
Glu Ser Lys Leu Ser Lys Thr Phe Asn Tyr Thr Thr Ser Lys Thr Val
145                 150                 155                 160

Ser Lys Thr Asp Asn Phe Lys Phe Gly Glu Lys Ile Gly Val Lys Thr
            165                 170                 175

Ser Phe Lys Val Gly Leu Glu Ala Ile Ala Asp Ser Lys Val Glu Thr
        180                 185                 190

Ser Phe Glu Phe Asn Ala Glu Gln Gly Trp Ser Asn Thr Asn Ser Thr
    195                 200                 205

Thr Glu Thr Lys Gln Glu Ser Thr Thr Tyr Thr Ala Thr Val Ser Pro
210                 215                 220

Gln Thr Lys Lys Arg Leu Phe Leu Asp Val Leu Gly Ser Gln Ile Asp
225                 230                 235                 240

Ile Pro Tyr Glu Gly Lys Ile Tyr Met Glu Tyr Asp Ile Glu Leu Met
            245                 250                 255

Gly Phe Leu Arg Tyr Thr Gly Asn Ala Arg Glu Asp His Thr Glu Asp
        260                 265                 270

Arg Pro Thr Val Lys Leu Lys Phe Gly Lys Asn Gly Met Ser Ala Glu
    275                 280                 285

Glu His Leu Lys Asp Leu Tyr Ser His Lys Asn Ile Asn Gly Tyr Ser
290                 295                 300

Glu Trp Asp Trp Lys Trp Val Asp Glu Lys Phe Gly Tyr Leu Phe Lys
305                 310                 315                 320

Asn Ser Tyr Asp Ala Leu Thr Ser Arg Lys Leu Gly Ile Ile Lys
            325                 330                 335

Gly Ser Phe Thr Asn Ile Asn Gly Thr Lys Ile Val Ile Arg Glu Gly
        340                 345                 350

Lys Glu Ile Pro Leu Pro Asp Lys Lys Arg Gly Lys Arg Ser Val
    355                 360                 365

Asp Ser Leu Asp Ala Arg Leu Gln Asn Glu Gly Ile Arg Ile Glu Asn
370                 375                 380

Ile Glu Thr Gln Asp Val Pro Gly Phe Arg Leu Asn Ser Ile Thr Tyr
385                 390                 395                 400

Asn Asp Lys Lys Leu Ile Leu Ile Asn Asn Ile
            405                 410
```

<210> SEQ ID NO 12
<211> LENGTH: 411
<212> TYPE: PRT
<213> ORGANISM: Artificial sequence
<220> FEATURE:
<223> OTHER INFORMATION: Completely synthesized.
<220> FEATURE:
<221> NAME/KEY: MISC_FEATURE
<222> LOCATION: (259)..(259)
<223> OTHER INFORMATION: Xaa at position 259 is ala, cys, asp, glu, phe,
gly, his, ile, lys, leu, met, asn, pro, gln, arg, ser, thr, val,
trp, or tyr.

<400> SEQUENCE: 12

```
Thr Asn Leu Glu Glu Gly Gly Tyr Ala Asn His Asn Asn Ala Ser Ser
1               5                   10                  15

Ile Lys Ile Phe Gly Tyr Glu Asp Asn Glu Asp Leu Lys Ala Lys Ile
            20                  25                  30

Ile Gln Asp Pro Glu Phe Ile Arg Asn Trp Ala Asn Val Ala His Ser
        35                  40                  45

Leu Gly Phe Gly Trp Cys Gly Gly Thr Ala Asn Pro Asn Val Gly Gln
    50                  55                  60
```

```
Gly Phe Glu Phe Lys Arg Glu Val Gly Ala Gly Lys Val Ser Tyr
 65                  70                  75                  80

Leu Leu Ser Ala Arg Tyr Asn Pro Asn Asp Pro Tyr Ala Ser Gly Tyr
                 85                  90                  95

Arg Ala Lys Asp Arg Leu Ser Met Lys Ile Ser Asn Val Arg Phe Val
            100                 105                 110

Ile Asp Asn Asp Ser Ile Lys Leu Gly Thr Pro Lys Val Lys Lys Leu
        115                 120                 125

Ala Pro Leu Asn Ser Ala Ser Phe Asp Leu Ile Asn Glu Ser Lys Thr
    130                 135                 140

Glu Ser Lys Leu Ser Lys Thr Phe Asn Tyr Thr Thr Ser Lys Thr Val
145                 150                 155                 160

Ser Lys Thr Asp Asn Phe Lys Phe Gly Glu Lys Ile Gly Val Lys Thr
                165                 170                 175

Ser Phe Lys Val Gly Leu Glu Ala Ile Ala Asp Ser Lys Val Glu Thr
            180                 185                 190

Ser Phe Glu Phe Asn Ala Glu Gln Gly Trp Ser Asn Thr Asn Ser Thr
        195                 200                 205

Thr Glu Thr Lys Gln Glu Ser Thr Thr Tyr Thr Ala Thr Val Ser Pro
    210                 215                 220

Gln Thr Lys Lys Arg Leu Phe Leu Asp Val Leu Gly Ser Gln Ile Asp
225                 230                 235                 240

Ile Pro Tyr Glu Gly Lys Ile Tyr Met Glu Tyr Asp Ile Glu Leu Met
                245                 250                 255

Gly Phe Xaa Arg Tyr Thr Gly Asn Ala Arg Glu Asp His Thr Glu Asp
            260                 265                 270

Arg Pro Thr Val Lys Leu Lys Phe Gly Lys Asn Gly Met Ser Ala Glu
        275                 280                 285

Glu His Leu Lys Asp Leu Tyr Ser His Lys Asn Ile Asn Gly Tyr Ser
    290                 295                 300

Glu Trp Asp Trp Lys Trp Val Asp Glu Lys Phe Gly Tyr Leu Phe Lys
305                 310                 315                 320

Asn Ser Tyr Asp Ala Leu Thr Ser Arg Lys Leu Gly Gly Ile Ile Lys
                325                 330                 335

Gly Ser Phe Thr Asn Ile Asn Gly Thr Lys Ile Val Ile Arg Glu Gly
            340                 345                 350

Lys Glu Ile Pro Leu Pro Asp Lys Lys Arg Gly Lys Arg Ser Val
    355                 360                 365

Asp Ser Leu Asp Ala Arg Leu Gln Asn Glu Gly Ile Arg Ile Glu Asn
370                 375                 380

Ile Glu Thr Gln Asp Val Pro Gly Phe Arg Leu Asn Ser Ile Thr Tyr
385                 390                 395                 400

Asn Asp Lys Lys Leu Ile Leu Ile Asn Asn Ile
                405                 410

<210> SEQ ID NO 13
<211> LENGTH: 411
<212> TYPE: PRT
<213> ORGANISM: Artificial sequence
<220> FEATURE:
<223> OTHER INFORMATION: Completely synthesized.
<220> FEATURE:
<221> NAME/KEY: MISC_FEATURE
<222> LOCATION: (260)..(260)
<223> OTHER INFORMATION: Xaa at position 260 is ala, cys, asp, glu, phe,
      gly, his, ile, lys, leu, met, asn, pro, gln, arg, ser, thr, val,
      trp, or tyr.
```

<400> SEQUENCE: 13

```
Thr Asn Leu Glu Glu Gly Gly Tyr Ala Asn His Asn Asn Ala Ser Ser
  1               5                  10                  15
Ile Lys Ile Phe Gly Tyr Glu Asp Asn Glu Asp Leu Lys Ala Lys Ile
             20                  25                  30
Ile Gln Asp Pro Glu Phe Ile Arg Asn Trp Ala Asn Val Ala His Ser
         35                  40                  45
Leu Gly Phe Gly Trp Cys Gly Gly Thr Ala Asn Pro Asn Val Gly Gln
     50                  55                  60
Gly Phe Glu Phe Lys Arg Glu Val Gly Ala Gly Lys Val Ser Tyr
 65                  70                  75                  80
Leu Leu Ser Ala Arg Tyr Asn Pro Asn Asp Pro Tyr Ala Ser Gly Tyr
                 85                  90                  95
Arg Ala Lys Asp Arg Leu Ser Met Lys Ile Ser Asn Val Arg Phe Val
                100                 105                 110
Ile Asp Asn Asp Ser Ile Lys Leu Gly Thr Pro Lys Val Lys Lys Leu
            115                 120                 125
Ala Pro Leu Asn Ser Ala Ser Phe Asp Leu Ile Asn Glu Ser Lys Thr
        130                 135                 140
Glu Ser Lys Leu Ser Lys Thr Phe Asn Tyr Thr Thr Ser Lys Thr Val
145                 150                 155                 160
Ser Lys Thr Asp Asn Phe Lys Phe Gly Glu Lys Ile Gly Val Lys Thr
                165                 170                 175
Ser Phe Lys Val Gly Leu Glu Ala Ile Ala Asp Ser Lys Val Glu Thr
            180                 185                 190
Ser Phe Glu Phe Asn Ala Glu Gln Gly Trp Ser Asn Thr Asn Ser Thr
        195                 200                 205
Thr Glu Thr Lys Gln Glu Ser Thr Thr Tyr Thr Ala Thr Val Ser Pro
    210                 215                 220
Gln Thr Lys Lys Arg Leu Phe Leu Asp Val Leu Gly Ser Gln Ile Asp
225                 230                 235                 240
Ile Pro Tyr Glu Gly Lys Ile Tyr Met Glu Tyr Asp Ile Glu Leu Met
                245                 250                 255
Gly Phe Leu Xaa Tyr Thr Gly Asn Ala Arg Glu Asp His Thr Glu Asp
            260                 265                 270
Arg Pro Thr Val Lys Leu Lys Phe Gly Lys Asn Gly Met Ser Ala Glu
        275                 280                 285
Glu His Leu Lys Asp Leu Tyr Ser His Lys Asn Ile Asn Gly Tyr Ser
    290                 295                 300
Glu Trp Asp Trp Lys Trp Val Asp Glu Lys Phe Gly Tyr Leu Phe Lys
305                 310                 315                 320
Asn Ser Tyr Asp Ala Leu Thr Ser Arg Lys Leu Gly Gly Ile Ile Lys
                325                 330                 335
Gly Ser Phe Thr Asn Ile Asn Gly Thr Lys Ile Val Ile Arg Glu Gly
            340                 345                 350
Lys Glu Ile Pro Leu Pro Asp Lys Arg Arg Gly Lys Arg Ser Val
        355                 360                 365
Asp Ser Leu Asp Ala Arg Leu Gln Asn Glu Gly Ile Arg Ile Glu Asn
    370                 375                 380
Ile Glu Thr Gln Asp Val Pro Gly Phe Arg Leu Asn Ser Ile Thr Tyr
385                 390                 395                 400
Asn Asp Lys Lys Leu Ile Leu Ile Asn Asn Ile
```

-continued

<210> SEQ ID NO 14
<211> LENGTH: 411
<212> TYPE: PRT
<213> ORGANISM: Artificial sequence
<220> FEATURE:
<223> OTHER INFORMATION: Completely synthesized.
<220> FEATURE:
<221> NAME/KEY: MISC_FEATURE
<222> LOCATION: (261)..(261)
<223> OTHER INFORMATION: Xaa at position 261 is ala, cys, asp, glu, phe,
      gly, his, ile, lys, leu, met, asn, pro, gln, arg, ser, thr, val,
      trp, or tyr.

<400> SEQUENCE: 14

```
Thr Asn Leu Glu Glu Gly Gly Tyr Ala Asn His Asn Asn Ala Ser Ser
  1               5                  10                  15

Ile Lys Ile Phe Gly Tyr Glu Asp Asn Glu Asp Leu Lys Ala Lys Ile
             20                  25                  30

Ile Gln Asp Pro Glu Phe Ile Arg Asn Trp Ala Asn Val Ala His Ser
         35                  40                  45

Leu Gly Phe Gly Trp Cys Gly Gly Thr Ala Asn Pro Asn Val Gly Gln
     50                  55                  60

Gly Phe Glu Phe Lys Arg Glu Val Gly Ala Gly Lys Val Ser Tyr
 65                  70                  75                  80

Leu Leu Ser Ala Arg Tyr Asn Pro Asn Asp Pro Tyr Ala Ser Gly Tyr
                 85                  90                  95

Arg Ala Lys Asp Arg Leu Ser Met Lys Ile Ser Asn Val Arg Phe Val
                100                 105                 110

Ile Asp Asn Asp Ser Ile Lys Leu Gly Thr Pro Lys Val Lys Lys Leu
            115                 120                 125

Ala Pro Leu Asn Ser Ala Ser Phe Asp Leu Ile Asn Glu Ser Lys Thr
        130                 135                 140

Glu Ser Lys Leu Ser Lys Thr Phe Asn Tyr Thr Thr Ser Lys Thr Val
145                 150                 155                 160

Ser Lys Thr Asp Asn Phe Lys Phe Gly Glu Lys Ile Gly Val Lys Thr
                165                 170                 175

Ser Phe Lys Val Gly Leu Glu Ala Ile Ala Asp Ser Lys Val Glu Thr
            180                 185                 190

Ser Phe Glu Phe Asn Ala Glu Gln Gly Trp Ser Asn Thr Asn Ser Thr
        195                 200                 205

Thr Glu Thr Lys Gln Glu Ser Thr Thr Tyr Thr Ala Thr Val Ser Pro
    210                 215                 220

Gln Thr Lys Lys Arg Leu Phe Leu Asp Val Leu Gly Ser Gln Ile Asp
225                 230                 235                 240

Ile Pro Tyr Glu Gly Lys Ile Tyr Met Glu Tyr Asp Ile Glu Leu Met
                245                 250                 255

Gly Phe Leu Arg Xaa Thr Gly Asn Ala Arg Glu Asp His Thr Glu Asp
            260                 265                 270

Arg Pro Thr Val Lys Leu Lys Phe Gly Lys Asn Gly Met Ser Ala Glu
        275                 280                 285

Glu His Leu Lys Asp Leu Tyr Ser His Lys Asn Ile Asn Gly Tyr Ser
    290                 295                 300

Glu Trp Asp Trp Lys Trp Val Asp Glu Lys Phe Gly Tyr Leu Phe Lys
305                 310                 315                 320

Asn Ser Tyr Asp Ala Leu Thr Ser Arg Lys Leu Gly Gly Ile Ile Lys
```

```
                    325                 330                 335
Gly Ser Phe Thr Asn Ile Asn Gly Thr Lys Ile Val Ile Arg Glu Gly
            340                 345                 350

Lys Glu Ile Pro Leu Pro Asp Lys Lys Arg Arg Gly Lys Arg Ser Val
        355                 360                 365

Asp Ser Leu Asp Ala Arg Leu Gln Asn Glu Gly Ile Arg Ile Glu Asn
    370                 375                 380

Ile Glu Thr Gln Asp Val Pro Gly Phe Arg Leu Asn Ser Ile Thr Tyr
385                 390                 395                 400

Asn Asp Lys Lys Leu Ile Leu Ile Asn Asn Ile
                405                 410

<210> SEQ ID NO 15
<211> LENGTH: 411
<212> TYPE: PRT
<213> ORGANISM: Artificial sequence
<220> FEATURE:
<223> OTHER INFORMATION: Completely synthesized.
<220> FEATURE:
<221> NAME/KEY: MISC_FEATURE
<222> LOCATION: (264)..(264)
<223> OTHER INFORMATION: Xaa at position 264 is ala, cys, asp, glu, phe,
      gly, his, ile, lys, leu, met, asn, pro, gln, arg, ser, thr, val,
      trp, or tyr.

<400> SEQUENCE: 15

Thr Asn Leu Glu Glu Gly Gly Tyr Ala Asn His Asn Asn Ala Ser Ser
1               5                   10                  15

Ile Lys Ile Phe Gly Tyr Glu Asp Asn Glu Asp Leu Lys Ala Lys Ile
            20                  25                  30

Ile Gln Asp Pro Glu Phe Ile Arg Asn Trp Ala Asn Val Ala His Ser
        35                  40                  45

Leu Gly Phe Gly Trp Cys Gly Gly Thr Ala Asn Pro Asn Val Gly Gln
    50                  55                  60

Gly Phe Glu Phe Lys Arg Glu Val Gly Ala Gly Lys Val Ser Tyr
65                  70                  75                  80

Leu Leu Ser Ala Arg Tyr Asn Pro Asn Asp Pro Tyr Ala Ser Gly Tyr
                85                  90                  95

Arg Ala Lys Asp Arg Leu Ser Met Lys Ile Ser Asn Val Arg Phe Val
            100                 105                 110

Ile Asp Asn Asp Ser Ile Lys Leu Gly Thr Pro Lys Val Lys Lys Leu
        115                 120                 125

Ala Pro Leu Asn Ser Ala Ser Phe Asp Leu Ile Asn Glu Ser Lys Thr
    130                 135                 140

Glu Ser Lys Leu Ser Lys Thr Phe Asn Tyr Thr Thr Ser Lys Thr Val
145                 150                 155                 160

Ser Lys Thr Asp Asn Phe Lys Phe Gly Glu Lys Ile Gly Val Lys Thr
                165                 170                 175

Ser Phe Lys Val Gly Leu Glu Ala Ile Ala Asp Ser Lys Val Glu Thr
            180                 185                 190

Ser Phe Glu Phe Asn Ala Glu Gln Gly Trp Ser Asn Thr Asn Ser Thr
        195                 200                 205

Thr Glu Thr Lys Gln Glu Ser Thr Thr Tyr Thr Ala Thr Val Ser Pro
    210                 215                 220

Gln Thr Lys Lys Arg Leu Phe Leu Asp Val Leu Gly Ser Gln Ile Asp
225                 230                 235                 240

Ile Pro Tyr Glu Gly Lys Ile Tyr Met Glu Tyr Asp Ile Glu Leu Met
```

-continued

```
                    245                 250                 255
Gly Phe Leu Arg Tyr Thr Gly Xaa Ala Arg Glu Asp His Thr Glu Asp
                260                 265                 270

Arg Pro Thr Val Lys Leu Lys Phe Gly Lys Asn Gly Met Ser Ala Glu
            275                 280                 285

Glu His Leu Lys Asp Leu Tyr Ser His Lys Asn Ile Asn Gly Tyr Ser
        290                 295                 300

Glu Trp Asp Trp Lys Trp Val Asp Glu Lys Phe Gly Tyr Leu Phe Lys
305                 310                 315                 320

Asn Ser Tyr Asp Ala Leu Thr Ser Arg Lys Leu Gly Ile Ile Lys
                325                 330                 335

Gly Ser Phe Thr Asn Ile Asn Gly Thr Lys Ile Val Ile Arg Glu Gly
                340                 345                 350

Lys Glu Ile Pro Leu Pro Asp Lys Lys Arg Arg Gly Lys Arg Ser Val
            355                 360                 365

Asp Ser Leu Asp Ala Arg Leu Gln Asn Glu Gly Ile Arg Ile Glu Asn
        370                 375                 380

Ile Glu Thr Gln Asp Val Pro Gly Phe Arg Leu Asn Ser Ile Thr Tyr
385                 390                 395                 400

Asn Asp Lys Lys Leu Ile Leu Ile Asn Asn Ile
                405                 410

<210> SEQ ID NO 16
<211> LENGTH: 411
<212> TYPE: PRT
<213> ORGANISM: Artificial sequence
<220> FEATURE:
<223> OTHER INFORMATION: Completely synthesized.
<220> FEATURE:
<221> NAME/KEY: MISC_FEATURE
<222> LOCATION: (268)..(268)
<223> OTHER INFORMATION: Xaa at position 268 is ala, cys, asp, glu, phe,
      gly, his, ile, lys, leu, met, asn, pro, gln, arg, ser, thr, val,
      trp, or tyr.

<400> SEQUENCE: 16

Thr Asn Leu Glu Glu Gly Gly Tyr Ala Asn His Asn Asn Ala Ser Ser
1               5                   10                  15

Ile Lys Ile Phe Gly Tyr Glu Asp Asn Glu Asp Leu Lys Ala Lys Ile
                20                  25                  30

Ile Gln Asp Pro Glu Phe Ile Arg Asn Trp Ala Asn Val Ala His Ser
            35                  40                  45

Leu Gly Phe Gly Trp Cys Gly Gly Thr Ala Asn Pro Asn Val Gly Gln
        50                  55                  60

Gly Phe Glu Phe Lys Arg Glu Val Gly Ala Gly Lys Val Ser Tyr
65                  70                  75                  80

Leu Leu Ser Ala Arg Tyr Asn Pro Asn Asp Pro Tyr Ala Ser Gly Tyr
                85                  90                  95

Arg Ala Lys Asp Arg Leu Ser Met Lys Ile Ser Asn Val Arg Phe Val
            100                 105                 110

Ile Asp Asn Asp Ser Ile Lys Leu Gly Thr Pro Lys Val Lys Lys Leu
        115                 120                 125

Ala Pro Leu Asn Ser Ala Ser Phe Asp Leu Ile Asn Glu Ser Lys Thr
    130                 135                 140

Glu Ser Lys Leu Ser Lys Thr Phe Asn Tyr Thr Thr Ser Lys Thr Val
145                 150                 155                 160

Ser Lys Thr Asp Asn Phe Lys Phe Gly Glu Lys Ile Gly Val Lys Thr
```

-continued

```
                165                 170                 175
Ser Phe Lys Val Gly Leu Glu Ala Ile Ala Asp Ser Lys Val Glu Thr
            180                 185                 190

Ser Phe Glu Phe Asn Ala Glu Gln Gly Trp Ser Asn Thr Asn Ser Thr
            195                 200                 205

Thr Glu Thr Lys Gln Glu Ser Thr Thr Tyr Thr Ala Thr Val Ser Pro
        210                 215                 220

Gln Thr Lys Lys Arg Leu Phe Leu Asp Val Leu Gly Ser Gln Ile Asp
225                 230                 235                 240

Ile Pro Tyr Glu Gly Lys Ile Tyr Met Glu Tyr Asp Ile Glu Leu Met
                245                 250                 255

Gly Phe Leu Arg Tyr Thr Gly Asn Ala Arg Glu Xaa His Thr Glu Asp
            260                 265                 270

Arg Pro Thr Val Lys Leu Lys Phe Gly Lys Asn Gly Met Ser Ala Glu
        275                 280                 285

Glu His Leu Lys Asp Leu Tyr Ser His Lys Asn Ile Asn Gly Tyr Ser
    290                 295                 300

Glu Trp Asp Trp Lys Trp Val Asp Glu Lys Phe Gly Tyr Leu Phe Lys
305                 310                 315                 320

Asn Ser Tyr Asp Ala Leu Thr Ser Arg Lys Leu Gly Ile Ile Lys
                325                 330                 335

Gly Ser Phe Thr Asn Ile Asn Gly Thr Lys Ile Val Ile Arg Glu Gly
            340                 345                 350

Lys Glu Ile Pro Leu Pro Asp Lys Lys Arg Gly Lys Arg Ser Val
        355                 360                 365

Asp Ser Leu Asp Ala Arg Leu Gln Asn Glu Gly Ile Arg Ile Glu Asn
    370                 375                 380

Ile Glu Thr Gln Asp Val Pro Gly Phe Arg Leu Asn Ser Ile Thr Tyr
385                 390                 395                 400

Asn Asp Lys Lys Leu Ile Leu Ile Asn Asn Ile
                405                 410
```

<210> SEQ ID NO 17
<211> LENGTH: 411
<212> TYPE: PRT
<213> ORGANISM: Artificial sequence
<220> FEATURE:
<223> OTHER INFORMATION: Completely synthesized.
<220> FEATURE:
<221> NAME/KEY: MISC_FEATURE
<222> LOCATION: (269)..(269)
<223> OTHER INFORMATION: Xaa at position 269 is ala, cys, asp, glu, phe,
      gly, his, ile, lys, leu, met, asn, pro, gln, arg, ser, thr, val,
      trp, or tyr.

<400> SEQUENCE: 17

```
Thr Asn Leu Glu Glu Gly Gly Tyr Ala Asn His Asn Asn Ala Ser Ser
1               5                   10                  15

Ile Lys Ile Phe Gly Tyr Glu Asp Asn Glu Asp Leu Lys Ala Lys Ile
            20                  25                  30

Ile Gln Asp Pro Glu Phe Ile Arg Asn Trp Ala Asn Val Ala His Ser
        35                  40                  45

Leu Gly Phe Gly Trp Cys Gly Gly Thr Ala Asn Pro Asn Val Gly Gln
    50                  55                  60

Gly Phe Glu Phe Lys Arg Glu Val Gly Ala Gly Lys Val Ser Tyr
65                  70                  75                  80

Leu Leu Ser Ala Arg Tyr Asn Pro Asn Asp Pro Tyr Ala Ser Gly Tyr
```

-continued

```
                    85                  90                  95
Arg Ala Lys Asp Arg Leu Ser Met Lys Ile Ser Asn Val Arg Phe Val
                100                 105                 110
Ile Asp Asn Asp Ser Ile Lys Leu Gly Thr Pro Lys Val Lys Lys Leu
                115                 120                 125
Ala Pro Leu Asn Ser Ala Ser Phe Asp Leu Ile Asn Glu Ser Lys Thr
            130                 135                 140
Glu Ser Lys Leu Ser Lys Thr Phe Asn Tyr Thr Thr Ser Lys Thr Val
145                 150                 155                 160
Ser Lys Thr Asp Asn Phe Lys Phe Gly Glu Lys Ile Gly Val Lys Thr
                165                 170                 175
Ser Phe Lys Val Gly Leu Glu Ala Ile Ala Asp Ser Lys Val Glu Thr
                180                 185                 190
Ser Phe Glu Phe Asn Ala Glu Gln Gly Trp Ser Asn Thr Asn Ser Thr
            195                 200                 205
Thr Glu Thr Lys Gln Glu Ser Thr Thr Tyr Thr Ala Thr Val Ser Pro
        210                 215                 220
Gln Thr Lys Lys Arg Leu Phe Leu Asp Val Leu Gly Ser Gln Ile Asp
225                 230                 235                 240
Ile Pro Tyr Glu Gly Lys Ile Tyr Met Glu Tyr Asp Ile Glu Leu Met
                245                 250                 255
Gly Phe Leu Arg Tyr Thr Gly Asn Ala Arg Glu Asp Xaa Thr Glu Asp
                260                 265                 270
Arg Pro Thr Val Lys Leu Lys Phe Gly Lys Asn Gly Met Ser Ala Glu
                275                 280                 285
Glu His Leu Lys Asp Leu Tyr Ser His Lys Asn Ile Asn Gly Tyr Ser
        290                 295                 300
Glu Trp Asp Trp Lys Trp Val Asp Glu Lys Phe Gly Tyr Leu Phe Lys
305                 310                 315                 320
Asn Ser Tyr Asp Ala Leu Thr Ser Arg Lys Leu Gly Gly Ile Ile Lys
                325                 330                 335
Gly Ser Phe Thr Asn Ile Asn Gly Thr Lys Ile Val Ile Arg Glu Gly
            340                 345                 350
Lys Glu Ile Pro Leu Pro Asp Lys Lys Arg Arg Gly Lys Arg Ser Val
        355                 360                 365
Asp Ser Leu Asp Ala Arg Leu Gln Asn Glu Gly Ile Arg Ile Glu Asn
        370                 375                 380
Ile Glu Thr Gln Asp Val Pro Gly Phe Arg Leu Asn Ser Ile Thr Tyr
385                 390                 395                 400
Asn Asp Lys Lys Leu Ile Leu Ile Asn Asn Ile
                405                 410
```

<210> SEQ ID NO 18
<211> LENGTH: 411
<212> TYPE: PRT
<213> ORGANISM: Artificial sequence
<220> FEATURE:
<223> OTHER INFORMATION: Completely synthesized.
<220> FEATURE:
<221> NAME/KEY: MISC_FEATURE
<222> LOCATION: (270)..(270)
<223> OTHER INFORMATION: Xaa at position 270 is ala, cys, asp, glu, phe,
      gly, his, ile, lys, leu, met, asn, pro, gln, arg, ser, thr, val,
      trp, or tyr.

<400> SEQUENCE: 18

Thr Asn Leu Glu Glu Gly Gly Tyr Ala Asn His Asn Asn Ala Ser Ser

```
1               5                   10                  15
Ile Lys Ile Phe Gly Tyr Glu Asp Asn Glu Asp Leu Lys Ala Lys Ile
                20                  25                  30

Ile Gln Asp Pro Glu Phe Ile Arg Asn Trp Ala Asn Val Ala His Ser
                35                  40                  45

Leu Gly Phe Gly Trp Cys Gly Gly Thr Ala Asn Pro Asn Val Gly Gln
                50                  55                  60

Gly Phe Glu Phe Lys Arg Glu Val Gly Ala Gly Lys Val Ser Tyr
65                  70                  75                  80

Leu Leu Ser Ala Arg Tyr Asn Pro Asn Asp Pro Tyr Ala Ser Gly Tyr
                85                  90                  95

Arg Ala Lys Asp Arg Leu Ser Met Lys Ile Ser Asn Val Arg Phe Val
                100                 105                 110

Ile Asp Asn Asp Ser Ile Lys Leu Gly Thr Pro Lys Val Lys Lys Leu
                115                 120                 125

Ala Pro Leu Asn Ser Ala Ser Phe Asp Leu Ile Asn Glu Ser Lys Thr
                130                 135                 140

Glu Ser Lys Leu Ser Lys Thr Phe Asn Tyr Thr Thr Ser Lys Thr Val
145                 150                 155                 160

Ser Lys Thr Asp Asn Phe Lys Phe Gly Glu Lys Ile Gly Val Lys Thr
                165                 170                 175

Ser Phe Lys Val Gly Leu Glu Ala Ile Ala Asp Ser Lys Val Glu Thr
                180                 185                 190

Ser Phe Glu Phe Asn Ala Glu Gln Gly Trp Ser Asn Thr Asn Ser Thr
                195                 200                 205

Thr Glu Thr Lys Gln Glu Ser Thr Thr Tyr Thr Ala Thr Val Ser Pro
                210                 215                 220

Gln Thr Lys Lys Arg Leu Phe Leu Asp Val Leu Gly Ser Gln Ile Asp
225                 230                 235                 240

Ile Pro Tyr Glu Gly Lys Ile Tyr Met Glu Tyr Asp Ile Glu Leu Met
                245                 250                 255

Gly Phe Leu Arg Tyr Thr Gly Asn Ala Arg Glu Asp His Xaa Glu Asp
                260                 265                 270

Arg Pro Thr Val Lys Leu Lys Phe Gly Lys Asn Gly Met Ser Ala Glu
                275                 280                 285

Glu His Leu Lys Asp Leu Tyr Ser His Lys Asn Ile Asn Gly Tyr Ser
                290                 295                 300

Glu Trp Asp Trp Lys Trp Val Asp Glu Lys Phe Gly Tyr Leu Phe Lys
305                 310                 315                 320

Asn Ser Tyr Asp Ala Leu Thr Ser Arg Lys Leu Gly Gly Ile Ile Lys
                325                 330                 335

Gly Ser Phe Thr Asn Ile Asn Gly Thr Lys Ile Val Ile Arg Glu Gly
                340                 345                 350

Lys Glu Ile Pro Leu Pro Asp Lys Lys Arg Arg Gly Lys Arg Ser Val
                355                 360                 365

Asp Ser Leu Asp Ala Arg Leu Gln Asn Glu Gly Ile Arg Ile Glu Asn
                370                 375                 380

Ile Glu Thr Gln Asp Val Pro Gly Phe Arg Leu Asn Ser Ile Thr Tyr
385                 390                 395                 400

Asn Asp Lys Lys Leu Ile Leu Ile Asn Asn Ile
                405                 410
```

<210> SEQ ID NO 19

-continued

```
<211> LENGTH: 411
<212> TYPE: PRT
<213> ORGANISM: Artificial sequence
<220> FEATURE:
<223> OTHER INFORMATION: Completely synthesized.
<220> FEATURE:
<221> NAME/KEY: MISC_FEATURE
<222> LOCATION: (273)..(273)
<223> OTHER INFORMATION: Xaa at position 273 is ala, cys, asp, glu, phe,
      gly, his, ile, lys, leu, met, asn, pro, gln, arg, ser, thr, val,
      trp, or tyr.

<400> SEQUENCE: 19
```

Thr Asn Leu Glu Glu Gly Gly Tyr Ala Asn His Asn Asn Ala Ser Ser
1               5                   10                  15

Ile Lys Ile Phe Gly Tyr Glu Asp Asn Glu Asp Leu Lys Ala Lys Ile
            20                  25                  30

Ile Gln Asp Pro Glu Phe Ile Arg Asn Trp Ala Asn Val Ala His Ser
        35                  40                  45

Leu Gly Phe Gly Trp Cys Gly Gly Thr Ala Asn Pro Asn Val Gly Gln
    50                  55                  60

Gly Phe Glu Phe Lys Arg Glu Val Gly Ala Gly Lys Val Ser Tyr
65                  70                  75                  80

Leu Leu Ser Ala Arg Tyr Asn Pro Asn Asp Pro Tyr Ala Ser Gly Tyr
                85                  90                  95

Arg Ala Lys Asp Arg Leu Ser Met Lys Ile Ser Asn Val Arg Phe Val
            100                 105                 110

Ile Asp Asn Asp Ser Ile Lys Leu Gly Thr Pro Lys Val Lys Lys Leu
        115                 120                 125

Ala Pro Leu Asn Ser Ala Ser Phe Asp Leu Ile Asn Glu Ser Lys Thr
    130                 135                 140

Glu Ser Lys Leu Ser Lys Thr Phe Asn Tyr Thr Thr Ser Lys Thr Val
145                 150                 155                 160

Ser Lys Thr Asp Asn Phe Lys Phe Gly Glu Lys Ile Gly Val Lys Thr
                165                 170                 175

Ser Phe Lys Val Gly Leu Glu Ala Ile Ala Asp Ser Lys Val Glu Thr
            180                 185                 190

Ser Phe Glu Phe Asn Ala Glu Gln Gly Trp Ser Asn Thr Asn Ser Thr
        195                 200                 205

Thr Glu Thr Lys Gln Glu Ser Thr Thr Tyr Thr Ala Thr Val Ser Pro
    210                 215                 220

Gln Thr Lys Lys Arg Leu Phe Leu Asp Val Leu Gly Ser Gln Ile Asp
225                 230                 235                 240

Ile Pro Tyr Glu Gly Lys Ile Tyr Met Glu Tyr Asp Ile Glu Leu Met
                245                 250                 255

Gly Phe Leu Arg Tyr Thr Gly Asn Ala Arg Glu Asp His Thr Glu Asp
            260                 265                 270

Xaa Pro Thr Val Lys Leu Lys Phe Gly Lys Asn Gly Met Ser Ala Glu
        275                 280                 285

Glu His Leu Lys Asp Leu Tyr Ser His Lys Asn Ile Asn Gly Tyr Ser
    290                 295                 300

Glu Trp Asp Trp Lys Trp Val Asp Glu Lys Phe Gly Tyr Leu Phe Lys
305                 310                 315                 320

Asn Ser Tyr Asp Ala Leu Thr Ser Arg Lys Leu Gly Ile Ile Lys
                325                 330                 335

Gly Ser Phe Thr Asn Ile Asn Gly Thr Lys Ile Val Ile Arg Glu Gly
            340                 345                 350

```
Lys Glu Ile Pro Leu Pro Asp Lys Lys Arg Arg Gly Lys Arg Ser Val
            355                 360                 365

Asp Ser Leu Asp Ala Arg Leu Gln Asn Glu Gly Ile Arg Ile Glu Asn
            370                 375                 380

Ile Glu Thr Gln Asp Val Pro Gly Phe Arg Leu Asn Ser Ile Thr Tyr
385                 390                 395                 400

Asn Asp Lys Lys Leu Ile Leu Ile Asn Asn Ile
                405                 410

<210> SEQ ID NO 20
<211> LENGTH: 411
<212> TYPE: PRT
<213> ORGANISM: Artificial sequence
<220> FEATURE:
<223> OTHER INFORMATION: Completely synthesized.
<220> FEATURE:
<221> NAME/KEY: MISC_FEATURE
<222> LOCATION: (310)..(310)
<223> OTHER INFORMATION: Xaa at position 310 is ala, cys, asp, glu, phe,
      gly, his, ile, lys, leu, met, asn, pro, gln, arg, ser, thr, val,
      trp, or tyr.

<400> SEQUENCE: 20

Thr Asn Leu Glu Glu Gly Gly Tyr Ala Asn His Asn Asn Ala Ser Ser
1               5                   10                  15

Ile Lys Ile Phe Gly Tyr Glu Asp Asn Glu Asp Leu Lys Ala Lys Ile
            20                  25                  30

Ile Gln Asp Pro Glu Phe Ile Arg Asn Trp Ala Asn Val Ala His Ser
        35                  40                  45

Leu Gly Phe Gly Trp Cys Gly Gly Thr Ala Asn Pro Asn Val Gly Gln
50                  55                  60

Gly Phe Glu Phe Lys Arg Glu Val Gly Ala Gly Lys Val Ser Tyr
65                  70                  75                  80

Leu Leu Ser Ala Arg Tyr Asn Pro Asn Asp Pro Tyr Ala Ser Gly Tyr
                85                  90                  95

Arg Ala Lys Asp Arg Leu Ser Met Lys Ile Ser Asn Val Arg Phe Val
            100                 105                 110

Ile Asp Asn Asp Ser Ile Lys Leu Gly Thr Pro Lys Val Lys Lys Leu
        115                 120                 125

Ala Pro Leu Asn Ser Ala Ser Phe Asp Leu Ile Asn Glu Ser Lys Thr
130                 135                 140

Glu Ser Lys Leu Ser Lys Thr Phe Asn Tyr Thr Thr Ser Lys Thr Val
145                 150                 155                 160

Ser Lys Thr Asp Asn Phe Lys Phe Gly Glu Lys Ile Gly Val Lys Thr
                165                 170                 175

Ser Phe Lys Val Gly Leu Glu Ala Ile Ala Asp Ser Lys Val Glu Thr
            180                 185                 190

Ser Phe Glu Phe Asn Ala Glu Gln Gly Trp Ser Asn Thr Asn Ser Thr
        195                 200                 205

Thr Glu Thr Lys Gln Glu Ser Thr Thr Tyr Thr Ala Thr Val Ser Pro
210                 215                 220

Gln Thr Lys Lys Arg Leu Phe Leu Asp Val Leu Gly Ser Gln Ile Asp
225                 230                 235                 240

Ile Pro Tyr Glu Gly Lys Ile Tyr Met Glu Tyr Asp Ile Glu Leu Met
                245                 250                 255

Gly Phe Leu Arg Tyr Thr Gly Asn Ala Arg Glu Asp His Thr Glu Asp
            260                 265                 270
```

```
Arg Pro Thr Val Lys Leu Lys Phe Gly Lys Asn Gly Met Ser Ala Glu
            275                 280                 285

Glu His Leu Lys Asp Leu Tyr Ser His Lys Asn Ile Asn Gly Tyr Ser
        290                 295                 300

Glu Trp Asp Trp Lys Xaa Val Asp Glu Lys Phe Gly Tyr Leu Phe Lys
305                 310                 315                 320

Asn Ser Tyr Asp Ala Leu Thr Ser Arg Lys Leu Gly Ile Ile Lys
                325                 330                 335

Gly Ser Phe Thr Asn Ile Asn Gly Thr Lys Ile Val Ile Arg Glu Gly
            340                 345                 350

Lys Glu Ile Pro Leu Pro Asp Lys Lys Arg Arg Gly Lys Arg Ser Val
            355                 360                 365

Asp Ser Leu Asp Ala Arg Leu Gln Asn Glu Gly Ile Arg Ile Glu Asn
        370                 375                 380

Ile Glu Thr Gln Asp Val Pro Gly Phe Arg Leu Asn Ser Ile Thr Tyr
385                 390                 395                 400

Asn Asp Lys Lys Leu Ile Leu Ile Asn Asn Ile
                405                 410

<210> SEQ ID NO 21
<211> LENGTH: 384
<212> TYPE: PRT
<213> ORGANISM: Artificial sequence
<220> FEATURE:
<223> OTHER INFORMATION: Completely synthesized.

<400> SEQUENCE: 21

Thr Asn Leu Glu Glu Gly Gly Tyr Ala Asn His Asn Asn Ala Ser Ser
1               5                   10                  15

Ile Lys Ile Phe Gly Tyr Glu Asp Asn Glu Asp Leu Lys Ala Lys Ile
                20                  25                  30

Ile Gln Asp Pro Glu Phe Ile Arg Asn Trp Ala Asn Val Ala His Ser
            35                  40                  45

Leu Gly Phe Gly Trp Cys Gly Gly Thr Ala Asn Pro Asn Val Gly Gln
50                  55                  60

Gly Phe Glu Phe Lys Arg Glu Val Gly Ala Gly Lys Val Ser Tyr
65                  70                  75                  80

Leu Leu Ser Ala Arg Tyr Asn Pro Asn Asp Pro Tyr Ala Ser Gly Tyr
                85                  90                  95

Arg Ala Lys Asp Arg Leu Ser Met Lys Ile Ser Asn Val Arg Phe Val
            100                 105                 110

Ile Asp Asn Asp Ser Ile Lys Leu Gly Thr Pro Lys Val Lys Lys Leu
        115                 120                 125

Ala Pro Leu Asn Ser Ala Ser Phe Asp Leu Ile Asn Glu Ser Lys Thr
    130                 135                 140

Glu Ser Lys Leu Ser Lys Thr Phe Asn Tyr Thr Thr Ser Lys Thr Val
145                 150                 155                 160

Ser Lys Thr Asp Asn Phe Lys Phe Gly Glu Lys Glu Gln Gly Trp Ser
                165                 170                 175

Asn Thr Asn Ser Thr Thr Glu Thr Lys Gln Glu Ser Thr Thr Tyr Thr
            180                 185                 190

Ala Thr Val Ser Pro Gln Thr Lys Lys Arg Leu Phe Leu Asp Val Leu
        195                 200                 205

Gly Ser Gln Ile Asp Ile Pro Tyr Glu Gly Lys Ile Tyr Met Glu Tyr
    210                 215                 220
```

Asp Ile Glu Leu Met Gly Phe Leu Arg Tyr Thr Gly Asn Ala Arg Glu
225                 230                 235                 240

Asp His Thr Glu Asp Arg Pro Thr Val Lys Leu Lys Phe Gly Lys Asn
            245                 250                 255

Gly Met Ser Ala Glu Glu His Leu Lys Asp Leu Tyr Ser His Lys Asn
            260                 265                 270

Ile Asn Gly Tyr Ser Glu Trp Asp Trp Lys Trp Val Asp Glu Lys Phe
        275                 280                 285

Gly Tyr Leu Phe Lys Asn Ser Tyr Asp Ala Leu Thr Ser Arg Lys Leu
        290                 295                 300

Gly Gly Ile Ile Lys Gly Ser Phe Thr Asn Ile Asn Gly Thr Lys Ile
305                 310                 315                 320

Val Ile Arg Glu Gly Lys Glu Ile Pro Leu Pro Asp Lys Lys Arg Arg
                325                 330                 335

Gly Lys Arg Ser Val Asp Ser Leu Asp Ala Arg Leu Gln Asn Glu Gly
            340                 345                 350

Ile Arg Ile Glu Asn Ile Glu Thr Gln Asp Val Pro Gly Phe Arg Leu
        355                 360                 365

Asn Ser Ile Thr Tyr Asn Asp Lys Lys Leu Ile Leu Ile Asn Asn Ile
        370                 375                 380

<210> SEQ ID NO 22
<211> LENGTH: 392
<212> TYPE: PRT
<213> ORGANISM: Artificial sequence
<220> FEATURE:
<223> OTHER INFORMATION: Completely synthesized.

<400> SEQUENCE: 22

Thr Asn Leu Glu Glu Gly Gly Tyr Ala Asn His Asn Asn Ala Ser Ser
1               5                   10                  15

Ile Lys Ile Phe Gly Tyr Glu Asp Asn Glu Asp Leu Lys Ala Lys Ile
                20                  25                  30

Ile Gln Asp Pro Glu Phe Ile Arg Asn Trp Ala Asn Val Ala His Ser
            35                  40                  45

Leu Gly Phe Gly Trp Cys Gly Gly Thr Ala Asn Pro Asn Val Gly Gln
    50                  55                  60

Gly Phe Glu Phe Lys Arg Glu Val Gly Ala Gly Lys Val Ser Tyr
65                  70                  75                  80

Leu Leu Ser Ala Arg Tyr Asn Pro Asn Asp Pro Tyr Ala Ser Gly Tyr
                85                  90                  95

Arg Ala Lys Asp Arg Leu Ser Met Lys Ile Ser Asn Val Arg Phe Val
            100                 105                 110

Ile Asp Asn Asp Ser Ile Lys Leu Gly Thr Pro Lys Val Lys Lys Leu
        115                 120                 125

Ala Pro Leu Asn Ser Ala Ser Phe Asp Leu Ile Asn Glu Ser Lys Thr
    130                 135                 140

Glu Ser Lys Leu Ser Lys Thr Phe Asn Tyr Thr Thr Ser Lys Thr Val
145                 150                 155                 160

Ser Lys Thr Asp Asn Phe Lys Phe Gly Glu Lys Ile Gly Val Lys Glu
                165                 170                 175

Phe Asn Ala Glu Gln Gly Trp Ser Asn Thr Asn Ser Thr Thr Glu Thr
            180                 185                 190

Lys Gln Glu Ser Thr Thr Tyr Thr Ala Thr Val Ser Pro Gln Thr Lys
        195                 200                 205

```
Lys Arg Leu Phe Leu Asp Val Leu Gly Ser Gln Ile Asp Ile Pro Tyr
    210                 215                 220

Glu Gly Lys Ile Tyr Met Glu Tyr Asp Ile Glu Leu Met Gly Phe Leu
225                 230                 235                 240

Arg Tyr Thr Gly Asn Ala Arg Glu Asp His Thr Glu Asp Arg Pro Thr
                245                 250                 255

Val Lys Leu Lys Phe Gly Lys Asn Gly Met Ser Ala Glu Glu His Leu
            260                 265                 270

Lys Asp Leu Tyr Ser His Lys Asn Ile Asn Gly Tyr Ser Glu Trp Asp
        275                 280                 285

Trp Lys Trp Val Asp Glu Lys Phe Gly Tyr Leu Phe Lys Asn Ser Tyr
290                 295                 300

Asp Ala Leu Thr Ser Arg Lys Leu Gly Gly Ile Ile Lys Gly Ser Phe
305                 310                 315                 320

Thr Asn Ile Asn Gly Thr Lys Ile Val Ile Arg Glu Gly Lys Glu Ile
                325                 330                 335

Pro Leu Pro Asp Lys Lys Arg Gly Lys Arg Ser Val Asp Ser Leu
            340                 345                 350

Asp Ala Arg Leu Gln Asn Glu Gly Ile Arg Ile Glu Asn Ile Glu Thr
        355                 360                 365

Gln Asp Val Pro Gly Phe Arg Leu Asn Ser Ile Thr Tyr Asn Asp Lys
370                 375                 380

Lys Leu Ile Leu Ile Asn Asn Ile
385                 390

<210> SEQ ID NO 23
<211> LENGTH: 400
<212> TYPE: PRT
<213> ORGANISM: Artificial sequence
<220> FEATURE:
<223> OTHER INFORMATION: Completely synthesized.

<400> SEQUENCE: 23

Thr Asn Leu Glu Glu Gly Gly Tyr Ala Asn His Asn Asn Ala Ser Ser
1               5                   10                  15

Ile Lys Ile Phe Gly Tyr Glu Asp Asn Glu Asp Leu Lys Ala Lys Ile
            20                  25                  30

Ile Gln Asp Pro Glu Phe Ile Arg Asn Trp Ala Asn Val Ala His Ser
        35                  40                  45

Leu Gly Phe Gly Trp Cys Gly Gly Thr Ala Asn Pro Asn Val Gly Gln
    50                  55                  60

Gly Phe Glu Phe Lys Arg Glu Val Gly Ala Gly Lys Val Ser Tyr
65                  70                  75                  80

Leu Leu Ser Ala Arg Tyr Asn Pro Asn Asp Pro Tyr Ala Ser Gly Tyr
                85                  90                  95

Arg Ala Lys Asp Arg Leu Ser Met Lys Ile Ser Asn Val Arg Phe Val
            100                 105                 110

Ile Asp Asn Asp Ser Ile Lys Leu Gly Thr Pro Lys Val Lys Lys Leu
        115                 120                 125

Ala Pro Leu Asn Ser Ala Ser Phe Asp Leu Ile Asn Glu Ser Lys Thr
    130                 135                 140

Glu Ser Lys Leu Ser Lys Thr Phe Asn Tyr Thr Thr Ser Lys Thr Val
145                 150                 155                 160

Ser Lys Thr Asp Asn Phe Lys Phe Gly Glu Lys Ile Gly Val Lys Thr
                165                 170                 175
```

```
Ser Phe Lys Glu Thr Ser Phe Glu Phe Asn Ala Glu Gln Gly Trp Ser
            180                 185                 190

Asn Thr Asn Ser Thr Thr Glu Thr Lys Gln Glu Ser Thr Thr Tyr Thr
            195                 200                 205

Ala Thr Val Ser Pro Gln Thr Lys Lys Arg Leu Phe Leu Asp Val Leu
            210                 215                 220

Gly Ser Gln Ile Asp Ile Pro Tyr Glu Gly Lys Ile Tyr Met Glu Tyr
225                 230                 235                 240

Asp Ile Glu Leu Met Gly Phe Leu Arg Tyr Thr Gly Asn Ala Arg Glu
                245                 250                 255

Asp His Thr Glu Asp Arg Pro Thr Val Lys Leu Lys Phe Gly Lys Asn
            260                 265                 270

Gly Met Ser Ala Glu Glu His Leu Lys Asp Leu Tyr Ser His Lys Asn
            275                 280                 285

Ile Asn Gly Tyr Ser Glu Trp Asp Trp Lys Trp Val Asp Glu Lys Phe
            290                 295                 300

Gly Tyr Leu Phe Lys Asn Ser Tyr Asp Ala Leu Thr Ser Arg Lys Leu
305                 310                 315                 320

Gly Gly Ile Ile Lys Gly Ser Phe Thr Asn Ile Asn Gly Thr Lys Ile
                325                 330                 335

Val Ile Arg Glu Gly Lys Glu Ile Pro Leu Pro Asp Lys Lys Arg Arg
            340                 345                 350

Gly Lys Arg Ser Val Asp Ser Leu Asp Ala Arg Leu Gln Asn Glu Gly
            355                 360                 365

Ile Arg Ile Glu Asn Ile Glu Thr Gln Asp Val Pro Gly Phe Arg Leu
            370                 375                 380

Asn Ser Ile Thr Tyr Asn Asp Lys Lys Leu Ile Leu Ile Asn Asn Ile
385                 390                 395                 400
```

US 7,179,888 B2

ANTIGENIC, NON-TOXIC MUTANTS OF *CLOSTRIDIUM SEPTICUM* ALPHA TOXIN AND VACCINES, ANTIBODIES, SERA, AND METHODS OF TREATMENT THEREWITH

CROSS REFERENCE TO RELATED APPLICATIONS

The present application claims benefit of U.S. Provisional 60/304,527, filed Jul. 11, 2001 and U.S. Provisional 60/305, 725, filed Jul. 16, 2001, each of which is hereby explicitly incorporated herein by reference in its entirety.

STATEMENT REGARDING FEDERALLY SPONSORED RESEARCH OR DEVELOPMENT

Some aspects of this invention were made in the course of Grant AI 32097 awarded by the National Institutes of Health and therefore the Government has certain rights in some aspects of this invention.

BACKGROUND

Currently, there are no vaccines for protection against *Clostridium septicum* infection in humans. Alpha toxin is produced by *C. septicum* and is its main lethal factor. In humans, the population of at-risk individuals for a *C. septicum* infection includes colonic cancer patients, diabetics, leukemia patients, and neutropenics.

Vaccines for animals are available but currently are made from killed whole *C. septicum* cells which cannot be used in humans. Moreover, such whole-cell vaccines have several disadvantages even when used in animals. For example, when the vaccine is used in cattle, there is significant loss of prime cuts of beef since the vaccination site is the loin area which yields some of the most valuable cuts of meat, such as tenderloin steak. Since the whole-cell vaccination results in such economic losses, other vaccines which do not result in the destruction of this meat are desirable. Furthermore, the production of killed whole-cell vaccines is difficult since these vaccines need to be extensively quality-tested prior to use, and even then there can be vaccine failures. The problems associated with killed whole-cell vaccines could be eliminated by producing a vaccine containing an immunogen which can be easily quality-tested and which is genetically inactive.

DESCRIPTION OF THE INVENTION

The invention contemplated herein comprises a variety of *C. septicum* alpha toxin derivatives (mutants) which are deficient in at least one specific function required for toxicity such that they are useful as vaccines for both humans and animals including, for example, cattle, chickens, turkeys, ostriches, emu, ducks, horses, donkeys, mules, pigs, sheep, goats, antelope, buffalo, llamas, cats, lions, tigers, dogs, bears, guinea pigs, chinchillas, mink, ferrets, rodents, parrots, parakeets, peacocks, seals, sea lions, orcas, monkeys, chimpanzees, baboons, orangutans, gorillas, and other zoo and livestock animals.

The present invention comprises purified derivatives (mutants) of *C. septicum* alpha toxin which are defective in at least one of three aspects of the native toxin's cytolytic mechanism, including (1) receptor binding, (2) membrane insertion and pore formation, and (3) cellular activation. In a preferred embodiment, purified forms of these alpha toxin mutants, or antigenic fragments thereof, which have sufficiently diminished hemolytic activity and diminished receptor binding can be used as vaccines against *C. septicum* disease since alpha toxin is the only lethal factor produced by *C. septicum* and immunity to this toxin likely plays a major role in immunity to disease caused by *C. septicum*. Research using alpha toxin to immunize mice can protect the mice from challenge with a *C. septicum* infection. (Ballard, J., A. Bryant, D. Stephens, R. K. Tweten. 1992. Purification and Characterization of the Lethal Toxin (Alpha-Toxin) of *Clostridium septicum*. Infect. Immun. 63:784–790. Each alpha toxin mutant described herein can be produced and purified by standard methods well known to those of ordinary skill in the art. The complete amino acid sequence of the native *C. septicum* alpha toxin is shown as SEQ ID NO:. 1. The cDNA which encodes SEQ ID NO:. 1 is shown as SEQ ID NO: 2.

"Mutant amino acid sequence," "mutant protein" or "mutant polypeptide" refers to a polypeptide having an amino acid sequence which varies from a native sequence or is encoded by a nucleotide sequence intentionally made variant from a native sequence. "Mutant protein," "variant protein" or "mutein" means a protein comprising a mutant amino acid sequence and includes polypeptides which differ from the amino acid sequence of native *C. septicum* alpha toxin due to amino acid deletions, substitutions, or both. "Native sequence" refers to an amino acid or nucleic acid sequence which is identical to a wild-type or native from of the *C. septicum* alpha toxin gene or protein.

The mutants of the present invention preferably have at least one substituted amino acid in the receptor binding domains of the alpha toxin which include amino acid positions 53, 54, 62, 84–102, 259–274 and 309–315 of the sequence of the native alpha toxin as shown in SEQ ID NO: 1. Mutants may also have a substitution or deletion in the membrane penetrating and pore forming domain which includes amino acids 168–204 of the native alpha toxin. Mutants may comprise combinations of more than one of any of the substitutions and/or deletions described herein, including, but not limited to, two, three or four substitutions and/or deletions.

As noted above, the novel mutants contemplated herein comprise at least one amino acid substitution or deletion of the native *C. septicum* alpha toxin. For example, any one or more of the amino acids at positions 53, 54, 62, 84–102, 168, 170, 172, 174, 176, 178, 180, 182, 184, 186, 188, 190, 192, 194, 196, 198, 200, 202, 204, 259–274, or 309–315 (also referred to herein as "critical positions") of the amino acid sequence of native *C. septicum* alpha toxin (SEQ ID NO: 1) may be substituted with a different amino acid in the same position.

In particular, the invention comprises mutants wherein at least one of the following native amino acids has been replaced with a different amino acid: trp at position 53, cys at 54, val at 62, ala at 84, arg at 85, tyr at 86, asn at 87, pro at 88, asn at 89, asp at 90, pro at 91, tyr at 92, ala at 93, ser at 94, gly at 95, tyr at 96, arg at 97, ala at 98, lys at 99, asp at 100, arg at 101, leu at 102, phe at 168, glu at 170, ile at 172, val at 174, thr at 176, phe at 178, val at 180, leu at 182, ala at 184, ala at 186, ser at 188, val at 190, thr at 192, phe at 194, phe at 196, ala at 198, gln at 200, trp at 202, asn at 204, leu at 259, arg at 260, tyr at 261, thr at 262, gly at 263, asn at 264, ala at 265, arg at 266, glu at 267, asp at 268, his at 269, thr at 270, glu at 271, asp at 272, arg at 273, pro at 274, lys at 309, trp at 310, val at 311, asp at 312, gluat313, lys at 314, or phe at 315 (SEQ ID NO:3). In general, the substitute amino acid may be selected from the entire group of the twenty natural amino acids (see Table I), or from synthetic amino acids, however, the substitutions at positions 168, 170, 172, 174, 176, 178, 180, 182, 184, 186, 188, 190, 192, 194, 196, 198, 200, 202, 204, which generally are non-polar amino acids, will preferably be substituted with charged amino acids such as aspartic acid, glutamic acid, lysine, histidine, and arginine. Mutants comprising deletions of portions of the membrane penetrating domain include, for example, a modified *C. septicum* alpha toxin having a deletion of amino acid positions 172–198, 176–194, or 180–190, or of any five or more contiguous amino acids between and including positions 168–204 of the native *C. septicum* alpha toxin. An especially preferred embodiment comprises a mutant having at least one substitution in the receptor binding domain and a deletion in the membrane penetrating domain. The mutants of the present invention have diminished or entirely lack hemolytic activity compared to the native *C. septicum* alpha toxin, and in an especially preferred embodiment are antigenic, whereby vaccines produced from them induce anti-alpha toxin antibodies in vivo as explained in more detail below.

The diminished hemolytic activity of the mutants may be demonstrated using an assay for hemolytic activity, an assay for human folate receptor binding, or an assay for binding to SUP-T1 cells, as described elsewhere herein, or any other standard assay known in the art effective in assaying hemolytic activity of *C. septicum* alpha toxin.

As noted above, it is an object of the present invention to provide novel vaccines comprising the alpha toxin mutants described herein, or antigenic fragments thereof, which are capable of inducing production of protective antibodies directed against *C. septicum* alpha toxin when administered to animals or humans and thereby providing prophylaxis against infection by *C. septicum* disease states resulting from such infection, and/or from the alpha toxin itself. It is a particular aim of the present invention to provide such a vaccine that is relatively safe and simple to produce. Antibodies and antisera so raised are also provided capable of use in therapy for a least some, if not all, disease states, in which where alpha toxin is essential for the organism's effect or viability.

In further aspects of the present invention there is provided recombinant DNA which encode the mutants, or antigenic fragments thereof, of the invention, plasmids comprising such DNA and cell lines comprising these plasmids or the recombinant DNA itself such that expression of the mutants may be achieved. Such recombinant DNA is conveniently provided by PCR amplification of the DNA encoding for the desired sequence, using primers targeted at respective ends of the double stranded sequence of which it forms one half, using methods well known to those of ordinary skill in the art.

In a further aspect of the present invention there are provided antisera raised to the mutants, or antigenic fragments thereof, of the invention and antibodies derived therefrom. Furthermore, the present invention provides monoclonal antibodies to the mutants, or antigenic fragments thereof, of the invention and hybridoma cells for production thereof as described in more detail below.

The present invention further contemplates alpha toxin mutants which have additional substitutions which are conservative substitutions of amino acids which are not in the critical positions as described elsewhere herein (i.e., positions 53, 54, 62, 84–102, 168, 170, 172, 174, 176, 178, 180, 182, 184, 186, 188, 190, 192, 194, 196, 198, 200, 202, 204, 259–274, or 309–315), wherein such additional conservative substitutions do not adversely affect the antigenicity of the mutant.

By "conservative substitution" is meant the substitution of an amino acid by another one of the same class; the classes according to Table I.

TABLE I

| CLASS | AMINO ACID |
| --- | --- |
| Nonpolar: | Ala, Val, Leu, Ile, Pro, Met, Phe, Trp |
| Uncharged polar: | Gly, Ser, Thr, Cys, Tyr, Asn, Gln |
| Acidic: | Asp, Glu |
| Basic: | Lys, Arg, His |

Table I. Classes of amino acids suitable for conservative substitution.

As is well known to those skilled in the art, altering any given non-critical amino acid of a protein by conservative substitution may not significantly alter the activity of that protein because the side-chain of the amino acid which is inserted into the sequence may be able to form similar bonds and contacts as the side chain of the amino acid which has been substituted for.

Non-conservative substitutions (outside the classes of Table I) are possible provided that these do not interrupt with in immunogenicity of the polypeptide.

The polypeptides of the invention may be prepared synthetically, or more suitable, they are obtained using recombinant DNA technology. Thus, the invention further provides a nucleic acid which encodes any of the mutants of SEQ ID NO:3 which have at least one substitution and/or deletion as described herein.

Such nucleic acids may be incorporated into an expression vector, such as a plasmid, under the control of a promoter as understood in the art. The vector may include other structures as conventional in the art, such as signal sequences, leader sequences and enhancers, and can be used to transform a host cell, for example a prokaryotic cell such as *E. Coli* or a eukaryotic cell. Transformed cells can then be cultured and polypeptide of the invention recovered therefrom, either from the cells or from the culture medium, depending upon whether the desired product is secreted from the cell or not.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementary may be "partial," in which only some of the nucleic acids' bases are matched according to the base pairing rules. Or, there may be "complete" or "total" complementary between the nucleic acids. The degree of complementary between nucleic acid strands has significant effects on the efficiency and strength of hybridization between nucleic acid strands. This is of particular importance in amplification reactions, as well as detection methods which depend upon binding between nucleic acids.

Nucleic acids of the present invention are DNA sequences which hybridize to the DNA sequences which encode the mutant polypeptides described herein, or their complementary sequences, under conditions of high or low stringency and which encode proteins having diminished hemolytic activity and which preferably can stimulate antibodies against native alpha toxin.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein (expressly entirely incorporated herein by reference). The conditions of temperature and ionic strength determine the "stringency" of the hybridization.

In one embodiment, high stringency conditions are prehybridization and hybridization at 68° C., washing twice with 0.1×SSC, 0.1% SDS for 20 minutes at 22° C. and twice with 0.1×SSC, 0.1% SDS for 20 minutes at 50° C. Hybridization is preferably overnight.

In one example, low stringency conditions comprise conditions equivalent to binding or hybridization at 42° C. in a solution consisting of 5×SSPE (43.8 g/l NaCl, 6.9 g/l $NaH_2PO_4 \cdot H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; sigma) and 100 µg/ml denatured salmon sperm DNA] followed by washing in a solution comprising 5×SSPE, 0.1% SDS at 42° C. when a probe of about 500 nucleotides in length is employed.

In another embodiment, low stringency conditions are prehybridization and hybridization at 68° C., washing twice with 2×SSC, 0.1% SDS for 5 minutes at 22° C., and twice with 0.2×SSC, 0.1% SDS for 5 minutes at 22° C. Hybridization is preferably overnight.

In an alternative embodiment, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Souther blotting procedures.

The carrier material is then washed three times each for 15 minutes using 2×SSC, 0.2% SDS preferably at least 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

It is well known in the art that numerous equivalent conditions may be employed to comprise low stringency conditions; factors such as the length and nature (e.g., DNA, RNA, base composition) of the probe and nature of the target (e.g., DNA, RNA, base composition, present in solution or immobilized, etc.) And the concentration of the salts and other components (e.g., the presence or absence of formamide, dextran sulfate, polyethylene glycol) are considered and the hybridization solution may be varied to generate conditions of low stringency hybridization different form, but equivalent to, the above listed conditions. In addition, conditions which promote hybridization under conditions of high stringency (e.g., increasing the temperature of the hybridization and/or wash steps, the use of formamide in the hybridization solution, etc.) are also know in the art.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described above.

When used in reference to a single-stranded nucleic acid sequence, the term "substantially homologous" refers to any probe which can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (e.g., the strength of the association between the nucleic acids) is impacted by such factors as the degree of complementary between the nucleic acids, stringency of the conditions involved, the $T_m$ (melting temperature) of the formed hybrid, and the G:C ration within the nucleic acids. As used herein the term "stringency" is used in reference to the conditions of temperature, ionic strength, and the presence of other compounds such as organic solvents, under which nucleic acid hybridizations are conducted.

As used herein, the terms "cell," "cell line," and "cell culture" are used interchangeably and all such designations include progeny. The words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

As used herein, the term "vector" is used in reference to nucleic acid molecules that transfer DNA segment(s) from one cell to another. The term "vehicle" is sometimes used interchangeably with "vector".

The terms "recombinant DNA vector" as used herein refers to DNA sequences containing a desired coding sequence and appropriate DNA sequences necessary for the expression of the operably linked coding sequence in a particular host organism. DNA sequences necessary for expression in prokaryotes include a promoter, optionally and operator sequence, a ribosome binding site and possibly other sequences. Eukaryotic cells are known to utilize promoters, polyadenylation signals and enhancers. It is not intended that the term be limited to any particular type of vector. Rather, it is intended that the term encompass vectors that remain autonomous within host cells (e.g., plasmids), as well as vectors that result in the integration of foreign (e.g., recombinant nucleic acid sequences) into the genome of the host cell.

The term "expression vector" and "recombinant expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals. It is contemplated that the present invention encompasses expression vectors that are integrated into host cell genomes, as well as vectors that remain unintegrated into the host genome.

The terms "in operable combination," "in operable order," and "operably linked," as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The mutants described herein may be expressed in either prokaryotic or eukaryotic host cells. Nucleic acid encoding the mutants may be introduced into bacterial host cells by a number of means including transformation or transfection of bacterial cells made competent for transformation by treatment with calcium chloride or by electroporation. If the mutants are to be expressed in eukaryotic host cells, nucleic acid encoding the protein or toxin of interest may be introduced into eukaryotic host cells by a number of means including calcium phosphate co-precipitation, spheroplast fusion, electroporation, microinjection, lipofection, protoplast fusion, and retroviral infection, for example. When the eukaryotic host cell is a yeast cell, transformation may be affected by treatment of the host cells with lithium acetate or by electroporation, for example.

In a preferred version of the invention, the mutant is characterized as having at least one of (1) less than 25% of the hemolytic activity of wild type alpha toxin, (2) less than 25% of the hFR binding activity of wild type alpha toxin, or (3) less than 25% of the Sup-T1 cell binding activity of wild type alpha toxin, as measured by assays described herein.

In a more preferred version of the invention, the mutant has less than 25% of the hemolytic activity and less than 25% of the hFR binding activity of wild-type alpha toxin, as measured by assays described herein. More preferably, the mutant has less than 25% of the hemolytic activity, less than 25% of the hFR binding activity, and less than 25% of the Sup-T1 cell binding activity of wild type alpha toxin as measured by assays described herein.

In a more preferred version of the invention, the mutant has less than 10% of the hemolytic activity and less than 10% of the hFR binding activity of wild-type alpha toxin, as measured by assays described herein. More preferably, the mutant has less than 10% of the hemolytic activity, less than 10% of the hFR binding activity, and less than 10% of the Sup-T1 cell binding activity of wild type alpha toxin as measured by assays described herein.

More preferably, the mutant has less than 5% of the hemolytic activity and less than 5% of the hFR binding activity of wild-type alpha toxin, as measured by assays described herein. Even more preferably, the mutant has less than 5% of the hemolytic activity, less than 5% of the hFR binding activity, and less than 5% of the Sup-T1 cell binding activity of wild type alpha toxin as measured by assays described herein.

Even more preferably, the mutant has less than 0% of the hemolytic activity and less than 0% of the hFR binding activity of wild-type alpha toxin, as measured by assays described herein. Most preferably, the mutant has less than 0% of the hemolytic activity, less than 0% of the hFR binding activity, and less than 0% of the Sup-T1 cell binding activity of wild type alpha toxin as measured by assays described herein.

As previously explained, the present invention comprises a polypeptide with is a mutant version of *C. septicum* alpha toxin polypeptide which has at least one amino acid which is different from native *C. septicum* alpha toxin in at least one of positions 53, 54, 62, 84–102, 168, 170, 172, 174, 176, 178, 180, 182, 184, 186, 188, 190, 192, 194, 196, 198, 200, 202, 204, 259–274, or309–315 of the amino acid sequence of native *C. septicum* alpha toxin. Preferably, though not necessarily, the native amino acid is substituted, in the mutant, with an amino acid which is in a different class as defined in Table I. For example a nonpolar amino acid is preferably substituted with a charged, or uncharged polar, amino acid. An uncharged nonpolar amino acid is preferably replaced with a nonpolar or charged amino acid. An acidic amino acid is preferably replaced with a nonpolar, uncharged polar, or basic amino acid. A basic amino acid is preferably replaced with a nonpolar, uncharged polar, or acidic amino acid. As noted previously, amino acid positions 168, 170, 172, 174, 176, 178, 180, 182, 184, 186, 188, 190, 192, 194, 196, 198, 200, 202, 204 are preferably replaced with basic or acidic amino acids.

It is further contemplated that the present invention comprises mutants having amino acid substitutions which are one, two, three or four amino acid positions upstream or downstream of any of the amino acid positions 53, 54, 62, 84–102, 168, 170, 172, 174, 176, 178, 180, 182, 184, 186, 188, 190, 192, 194, 196, 198, 200, 202, 204, 259–274, or 309–315, as previously described herein.

More particularly, the present invention contemplates a mutant of *Clostridium septicum* alpha toxin which completely or partially lacks the toxicity of a native *C. septicum* alpha toxin, and preferably, is antigenic. In an especially preferred embodiment, *C. septicum* alpha toxin mutant has the same amino acid sequence as native *C. septicum* alpha toxin except the cysteine at position 54 has been substituted with another amino acid (SEQ ID NO:4). Alternatively, the *C. septicum* alpha toxin mutant has the same amino acid sequence as native *C. septicum* alpha toxin except the valine residue at position 62 is substituted (SEQ ID NO:5). In other especially preferred embodiments, the aspartic acid residue at position 90 is substituted (SEQ ID NO:6), the tyrosine residue at position 92 is substituted (SEQ ID NO:7), the tyrosine residue at position 96 is substituted (SEQ ID NO:8), arginine residue at position 97 is substituted (SEQ ID NO:9), the arginine residue at position 101 is substituted (SEQ ID NO: 10), the leucine residue at position 102 is substituted (SEQ ID NO: 11), the leucine residue at position 259 is substituted (SEQ ID NO:12), the arginine residue at position 260 is substituted (SEQ ID NO:13), the tyrosine residue at position 261 is substituted (SEQ ID NO:14), the asparagine residue at position 264 is substituted (SEQ ID NO:15), the aspartic acid residue at position 268 is substituted (SEQ ID NO:16), the histidine residue at position 269 is substituted (SEQ ID NO:17), the threonine at position 270 is substituted (SEQ ID NO:18), the arginine residue at position 273 is substituted (SEQ ID NO: 19), or the tryptophan residue at position 310 is substituted (SEQ ID NO:20). As noted above, the native amino acid may be substituted with any other amino acid which causes a diminishment in the hemolytic activity of the mutant as compared to the hemolytic activity of the native alpha toxin. Preferably the amino acid is replaced with an amino acid which is in a different class according to Table I, but it will be understood that any amino acid may be used as the substitute in the mutant which diminishes the hemolytic activity of the mutant toxin, especially to the degree as defined elsewhere herein, for example, from 0%–25% of the hemolytic activity of the native alpha toxin. Most preferably, the mutant alpha toxin comprises substitutions at positions 54, 96, 259, 264, 266, 268, 269, 273 and 310.

Preferably, the mutant of *C. septicum* alpha toxin has a substitution in at least one of positions noted herein, but alternatively, the *C. septicum* alpha toxin mutant may have at least two, three, four, or more of the substitutions described herein. Preferred combinations of substitutions include at least two substitutions selected from positions 54, 62, 90, 92, 96, 97, 101, 102, 259, 260, 261, 264, 266, 268, 269, 270, 273, and 310. Especially preferred combinations of substitutions include at least two substitutions selected from positions 54, 96, 259, 264, 266, 268, 269, 273 and 310.

As noted previously, in other mutants contemplated herein, the amino acid residues at positions 172–198 (SEQ ID NO: 21),176–194 (SEQ ID NO: 22), or 180–190 (SEQ ID NO:23), may be deleted, or at least five consecutive amino acid residues between positions 168–204, inclusive, may be deleted, as long as the deletion causes a diminishment in the hemolytic activity of the mutant as compared to the hemolytic activity of the native alpha toxin. Preferably the deletion diminishes the hemolytic activity of the mutant toxin to 0%–25% of the hemolytic activity of the native alpha toxin by disrupting the membrane, insertion and pore forming function of the mutant.

More particularly, the invention as contemplated herein is a mutant (mutein) of *C. septicum* alpha toxin polypeptide which comprises:

(a) a modified *C. septicum* alpha toxin polypeptide (SEQ ID NO :3) having at least one substituted amino acid which is different from native *C. septicum* alpha toxin in at least one of positions 53, 54, 62, 84–102, 168, 170, 172, 174, 176, 178, 180, 182, 184, 186, 188, 190, 192, 194, 196, 198, 200, 202, 204, 259–274, or 309–315 of the amino acid sequence of native *C. septicum* alpha toxin (SEQ ID NO:1), wherein:

the amino acid at position 53 is ala, cys, asp, glu, phe, gly, his, ile, lys, leu, met, asn, pro, gln, arg, ser, thr, val, trp, or tyr;

the amino acid at position 54 is ala, cys, asp, glu, phe, gly, his, ile, lys, leu, met, asn, pro, gln, arg, ser, thr, val, trp, or tyr;

the amino acid at position 62 is ala, cys, asp, glu, phe, gly, his, ile, lys, leu, met, asn, pro, gln, arg, ser, thr, val, trp, or tyr;

the amino acid at position 84 is ala, cys, asp, glu, phe, gly, his, ile, lys, leu, met, asn, pro, gln, arg, ser, thr, val, trp, or tyr;

the amino acid at position 85 is ala, cys, asp, glu, phe, gly, his, ile, lys, leu, met, asn, pro, gln, arg, ser, thr, val, trp, or tyr;

the amino acid at position 86 is ala, cys, asp, glu, phe, gly, his, ile, lys, leu, met, asn, pro, gln, arg, ser, thr, val, trp, or tyr;

the amino acid at position 87 is ala, cys, asp, glu, phe, gly, his, ile, lys, leu, met, asn, pro, gln, arg, ser, thr, val, trp, or tyr;

the amino acid at position 88 is ala, cys, asp, glu, phe, gly, his, ile, lys, leu, met, asn, pro, gln, arg, ser, thr, val, trp, or tyr;

the amino acid at position 89 is ala, cys, asp, glu, phe, gly, his, ile, lys, leu, met, asn, pro, gln, arg, ser, thr, val, trp, or tyr;

the amino acid at position 90 is ala, cys, asp, glu, phe, gly, his, ile, lys, leu, met, asn, pro, gln, arg, ser, thr, val, trp, or tyr;

the amino acid at position 91 is ala, cys, asp, glu, phe, gly, his, ile, lys, leu, met, asn, pro, gln, arg, ser, thr, val, trp, or tyr;

the amino acid at position 92 is ala, cys, asp, glu, phe, gly, his, ile, lys, leu, met, asn, pro, gln, arg, ser, thr, val, trp, or tyr;

the amino acid at position 93 is ala, cys, asp, glu, phe, gly, his, ile, lys, leu, met, asn, pro, gln, arg, ser, thr, val, trp, or tyr;

the amino acid at position 94 is ala, cys, asp, glu, phe, gly, his, ile, lys, leu, met, asn, pro, gln, arg, ser, thr, val, trp, or tyr;

the amino acid at position 95 is ala, cys, asp, glu, phe, gly, his, ile, lys, leu, met, asn, pro, gln, arg, ser, thr, val, trp, or tyr;

the amino acid at position 96 is ala, cys, asp, glu, phe, gly, his, ile, lys, leu, met, asn, pro, gln, arg, ser, thr, val, trp, or tyr;

the amino acid at position 97 is ala, cys, asp, glu, phe, gly, his, ile, lys, leu, met, asn, pro, gin, arg, ser, thr, val, trp, or tyr;

the amino acid at position 98 is ala, cys, asp, glu, phe, gly, his, ile, lys, leu, met, asn, pro, gin, arg, ser, thr, val, trp, or tyr;

the amino acid at position 99 is ala, cys, asp, glu, phe, gly, his, ile, lys, leu, met, asn, pro, gin, arg, ser, thr, val, trp, or tyr;

the amino acid at position 100 is ala, cys, asp, glu, phe, gly, his, ile, lys, leu, met, asn, pro, gin, arg, ser, thr, val, trp, or tyr;

the amino acid at position 101 is ala, cys, asp, glu, phe, gly, his, ile, lys, leu, met, asn, pro, gin, arg, ser, thr, val, trp, or tyr;

the amino acid at position 102 is ala, cys, asp, glu, phe, gly, his, ile, lys, leu, met, asn, pro, gin, arg, ser, thr, val, trp, or tyr;

the amino acid at position 168 is asp, glu, phe, his, lys, or arg;

the amino acid at position 170 is asp, glu, his, lys, or arg;

the amino acid at position 172 is asp, glu, his, ile, lys, or arg;

the amino acid at position 174 is asp, glu, his, lys, arg, or val;

the amino acid at position 176 is asp, glu, his, lys, arg, or, thr;

the amino acid at position 178 is asp, glu, phe, his, lys, or arg;

the amino acid at position 180 is asp, glu, his, lys, arg, or val;

the amino acid at position 182 is asp, glu, his, lys, arg, or leu;

the amino acid at position 184 is ala, asp, glu, his, lys, or arg;

the amino acid at position 186 is ala, asp, glu, his, lys, or arg;

the amino acid at position 188 is asp, glu, his, lys, arg, or ser;

the amino acid at position 190 is asp, glu, his, lys, arg, or val;

the amino acid at position 192 is asp, glu, his, lys, arg, or thr;

the amino acid at position 194 is asp, glu, phe, his, lys, or arg;

the amino acid at position 196 is asp, glu, phe, his, lys, or arg;

the amino acid at position 198 is ala, asp, glu, his, lys, or arg;

the amino acid at position 200 is asp, glu, his, lys, gln, or arg;

the amino acid at position 202 is asp, glu, his, lys, arg, or trp;

the amino acid at position 204 is asp, glu, his, lys, asn, or arg;

the amino acid at position 259 is ala, cys, asp, glu, phe, gly, his, ile, lys, leu, met, asn, pro, gln, arg, ser, thr, val, trp, or tyr;

the amino acid at position 260 is ala, cys, asp, glu, phe, gly, his, ile, lys, leu, met, asn, pro, gln, arg, ser, thr, val, trp, or tyr;

the amino acid at position 261 is ala, cys, asp, glu, phe, gly, his, ile, lys, leu, met, asn, pro, gln, arg, ser, thr, val, trp, or tyr;

the amino acid at position 262 is ala, cys, asp, glu, phe, gly, his, ile, lys, leu, met, asn, pro, gln, arg, ser, thr, val, trp, or tyr;

the amino acid at position 263 is ala, cys, asp, glu, phe, gly, his, ile, lys, leu, met, asn, pro, gln, arg, ser, thr, val, trp, or tyr;

the amino acid at position 264 is ala, cys, asp, glu, phe, gly, his, ile, lys, leu, met, asn, pro, gln, arg, ser, thr, val, trp, or tyr;

the amino acid at position 265 is ala, cys, asp, glu, phe, gly, his, ile, lys, leu, met, asn, pro, gln, arg, ser, thr, val, trp, or tyr;

the amino acid at position 266 is ala, cys, asp, glu, phe, gly, his, ile, lys, leu, met, asn, pro, gln, arg, ser, thr, val, trp, or tyr;

the amino acid at position 267 is ala, cys, asp, glu, phe, gly, his, ile, lys, leu, met, asn, pro, gln, arg, ser, thr, val, trp, or tyr;
the amino acid at position 268 is ala, cys, asp, glu, phe, gly, his, ile, lys, leu, met, asn, pro, gln, arg, ser, thr, val, trp, or tyr;
the amino acid at position 269 is ala, cys, asp, glu, phe, gly, his, ile, lys, leu, met, asn, pro, gln, arg, ser, thr, val, trp, or tyr;
the amino acid at position 270 is ala, cys, asp, glu, phe, gly, his, ile, lys, leu, met, asn, pro, gln, arg, ser, thr, val, trp, or tyr;
the amino acid at position 271 is ala, cys, asp, glu, phe, gly, his, ile, lys, leu, met, asn, pro, gln, arg, ser, thr, val, trp, or tyr;
the amino acid at position 272 is ala, cys, asp, glu, phe, gly, his, ile, lys, leu, met, asn, pro, gln, arg, ser, thr, val, trp, or tyr;
the amino acid at position 273 is ala, cys, asp, glu, phe, gly, his, ile, lys, leu, met, asn, pro, gln, arg, ser, thr, val, trp, or tyr;
the amino acid at position 274 is ala, cys, asp, glu, phe, gly, his, ile, lys, leu, met, asn, pro, gln, arg, ser, thr, val, trp, or tyr;
the amino acid at position 309 is ala, cys, asp, glu, phe, gly, his, ile, lys, leu, met, asn, pro, gln, arg, ser, thr, val, trp, or tyr;
the amino acid at position 310 is ala, cys, asp, glu, phe, gly, his, ile, lys, leu, met, asn, pro, gin, arg, ser, thr, val, trp, or tyr;
the amino acid at position 311 is ala, cys, asp, glu, phe, gly, his, ile, lys, leu, met, asn, pro, gin, arg, ser, thr, val, trp, or tyr;
the amino acid at position 312 is ala, cys, asp, glu, phe, gly, his, ile, lys, leu, met, asn, pro, gin, arg, ser, thr, val, trp, or tyr;
the amino acid at position 313 is ala, cys, asp, glu, phe, gly, his, ile, lys, leu, met, asn, pro, gin, arg, ser, thr, val, trp, or tyr;
the amino acid at position 314 is ala, cys, asp, glu, phe, gly, his, ile, lys, leu, met, asn, pro, gin, arg, ser, thr, val, trp, or tyr; and
the amino acid at position 315 is ala, cys, asp, glu, phe, gly, his, ile, lys, leu, met, asn, pro, gin, arg, ser, thr, val, trp, or tyr; or
(b) a modified *C. septicum* alpha toxin having a deletion of amino acid positions 172–198, 176–194, or 180–190, or of any five or more contiguous amino acids between and including positions 168–204 of the native *C. septicum* alpha toxin; and
wherein the mutant of (a) or (b) has diminished hemolytic activity compared to the native *C. septicum* alpha toxin.

METHODOLOGY

Bacterial Strains, Plasmids, Cell Lines, and Chemicals

Alpha toxin was cloned into the pET-22(b)+ expression vector (Novagen, Madison, Wis.) (designated pBRS10) and placed into BLR-DE3 cells for high-level expression as previously described by Sellman et al (Sellman, B. R., B. L. Kagan, et al. (1997). "Generation of a membrane-bound, oligomerized pre-pore complex is necessary for pore formation by *Clostridium septicum* alpha toxin." *Molec. Microbiol.* 23: 551–558.). The Sup-T1 cell line used for all flow cytometry was obtained from Dr. William Hildebrand at OUHSC. All chemicals were obtained from Sigma Chemical Company and all enzymes from Gibco BRL unless otherwise specified.

Generation of Point Mutations

All alanine and other point mutations were generated using a four-primer site-directed PCR mutagenesis procedure previously described by Ho et al. (Ho, S. N., H. D. Hunt, et al. (1989). "Site-directed mutagenesis by overlap extension using polymerase chain reaction." *Gene* 77: 51–59.) using pBRS 10 as the template. pfu turbo thermostable polymerase (Stratagene, La Jolla, Calif.) was used in place of taq. PCR overlap products were cleaned using the Quantum-Prep PCR Kleen Spin columns (Bio-Rad, Hercules, Calif.), digested with NcoI and XhoI, and ligated into pET-22(b)+ digested with NcoI and XhoI.

$AT^{C86A}$ was generated using the above procedure and the resulting plasmid was designated pBRS20. $AT^{T224C}$ was produced using this plasmid as template for use in the IAF-labeling reactions below.

Expression, Purification and Activation of Alpha Toxin

The growth and harvesting of *E. coli* BLR-DE3 carrying pBRS 10 was done according to Sellman et al (1997). The cell pellets were resuspended in 150 ml of buffer A (10 mM MES (2-(N-morpholino)ethanesulphonic acid) (Research Organics, Cleveland Ohio.), 150 mM NaCl, pH 6.5). Lysis of cells was carried out in an EmulsiFlex-C5 high pressure homogenizer (Avestin, Ottawa, ON, Canada) at 15,000 psi. Cell debris was pelleted by centrifugation at 15,000 rpm for 10 min. Purification of AT over a colbalt-chelating column and cation-exchange column was done as previously described (Sellman et al, 1997). Alpha toxin-containing fractions eluted from the cation-exchange column were placed into a Micro-ProDiCon System (Spectrum, Gardena, Calif.) with a 10,000 MWCO Micro-ProDiCon membrane (Spectrum) for simultaneous dialysis and concentration. Samples were dialyzed against 10 mM MES, 500 mM NaCl, 1 mM EDTA, pH 6.5 overnight at 4° C. Concentrated toxin was placed in 10% glycerol and stored at −70° C. Protein was quantified by protein assay (Bio-Rad Laboratories, Hercules, Calif.) using bovine serum albumin as the protein standard.

Activation of $AT^{pro}$ was accomplished using trypsin at 1:3500 (w/w) trypsin to toxin ratio. The trypsin and toxin were incubated at 37° C. for 30 min. The reaction was stopped with the addition of a 30-fold molar excess of the protease inhibitor TLCK.

Hemolytic Assays and $HD_{50}$ Determination

Lysis of erythrocytes was monitored by hemoglobin release. 20 µg AT in a total volume of 50 µl (4.2 pMol) was placed into the first well in a single row of a microtiter plate, with the wells prefilled with phosphate-buffered saline (PBS; 10 mM $NaHPO_4$ [pH 7.0], 5 mM KCl, 145 mM NaCl, 0.1% glucose) containing 0.01% trypsin. The toxin was carried through two-fold serial dilutions in the remaining wells of the row. 50 µl of erythrocytes in PBS ($\sim 10^8$ cells $ml^{-1}$) were added to each well and the plate was incubated at 37° C. for 1 hour. Following incubation, the plate was centrifuged at 1500 rpm for 5 min. to pellet any unlysed erythrocytes. 25 µl of the supernatant from each well was then removed and placed into the wells of a second microtiter plate containing 75 µl PBS. The plate was placed into an Opsys MR spectrophotometric plate reader (Dynex Technologies, town, state) and read at $A_{540}$ to quantify hemoglobin release.

For $HD_{50}$ determination, $A_{540}$ values were plotted against the amount toxin and a linear graph produced. The $HD_{50}$ value for wild-type was determined as the amount of toxin required to lyse 50% of the erythrocytes. Results for a number of mutants described herein are shown in Table II.

AT Labeling with n-ethylmaleimide

A 20-molar excess of n-ethylmaleimide (Molecular Probes, Eugene, Oreg.) was added to 2 μg AT and brought up to a total volume of 50 μl with double distilled water. The mixture was incubated at 37° C. for 2 hours.

Receptor Blots 64 ng purified human folate receptor (hFR) (a generous gift from Dr. Patrick Elwood, NIH) was separated on a 10% SDS-PAGE and blotted onto nitrocellulose. Human folate-binding proteins (hFR) are described in Elwood, P. C., Kane, M. A., Portillo, R. M. and Kolhouse, J. F., "The isolation, characterization, and comparison of the membrane-associated and slouble folate-binding proteins from human KB cells". *J. Biol. Chem.*(1986) Nov. 25; 261(33): 15416–23 and Gordon, V. M., K. L. Nelson, et al., "*Clostridium septicum* alpha toxin uses glycosylphosphatidylinositol-anchored proteins receptors." *J. Biol. Chem.*(1999) 274 (38): 27274–80.). Following blocking overnight in PBS-Tween 20 (0.05%) containing 10% fetal calf serum, the blots were probed with 20 nM of either wild-type or mutant toxin for 2 hours, followed by affinity-purified anti-AT antibody and a secondary antibody conjugated to horseradish peroxidase for development using the ECL+ chemiluminescent detection kit (Amersham Pharmacia, Piscataway, N.J.). Blots were exposed to film to visualize bands. Results for a number of mutants are shown in Table II.

Modification Of $AT^{T224C}$ with iodoacetamide-fluoroscein (IAF)

2 mg $AT^{T224C}$ was passed over a Sephadex G-50 column (1.5 cm inside diameter×20 cm) equilibrated in 50 mM HEPES, 500 mM NaCl, (pH 8.0) at room temperature to remove excess DTT. Protein concentration was determined by protein assay (Bio-Rad, Hercules, Calif.) and a 20-molar excess of IAF was added. The reaction proceeded in the dark for 2 h at room temperature and placed over a Sephadex G-50 column as described above to remove excess dye. IAF-labeled toxin was pooled, made 10% (v/v) in glycerol, quick-frozen in liquid nitrogen, and stored in −80° C. The labeling efficiency of the reaction was determined using an $\epsilon_{492nm}$ of 75,000 $M^{-1}$ $cm^{-1}$ for IAF (ref. Molecular Probes).

Flow Cytometry and $ID_{50}$ Determination

The ability of the individual point mutants to compete for binding with $AT^{T224C-IAF}$ (equally as hemolytic as wild type AT) to Sup-T1 cells was determined. 1 μg $AT^{T224C-IAF}$ was mixed with 100 ng, 500 ng, 1 μg, 5 μg or 20 μg of either unlabeled wild-type or mutant toxin and brought up to a final volume of 100 μl in ice-cold Hanks buffered saline solution (HBSS)(Bio-Whittaker, town, state). The reaction was added to $10^6$ Sup-T1 cells and incubated for 30 min at 4° C. The Sup-T1 cell line is available from the NIH AIDS Research and Reference Reagent Program and are derived from Non-Hodgkins's T-cell lymphoma isolated from a pleural effusion of an eight-year-old male and sub-cloned on soft agar. (Smith, S. D., et al. *Cancer Res.,* 44: 5657;(1984)). The cells were washed twice with 200 μl ice-cold HBSS and brought up to a final volume of 400 μl with ice-cold HBSS for analysis on a FACS Calibur (Flow Cytometry and Confocal Microscopy Laboratory, WMRI, OUHSC, Oklahoma City, Okla.).

For $ID_{50}$ determination, the percentage of cells remaining fluorosceinated was averaged for each amount of unlabeled toxin added in three separate experiments. The percents were then plotted versus amount toxin. From this graph, the amount of each mutant toxin required to compete for 50 percent binding ($ID_{50}$) to Sup-T1 cells was determined. The $ID_{50}$ values for the mutant toxins were then divided by the $ID_{50}$ for wild-type and taken to 1/x to obtain the final percent binding for each mutant. Results for a number of mutants are shown in Table II.

Sup-T1 Cell Viability Assay

One μg AT in a total volume of 20 μl was placed into the first well in a single row of a 96-well round-bottom plate, with the wells prefilled with 20 μl HBSS (Hanks Balanced Salt Solution). The toxin was carried through two-fold serial dilutions from wells 1 through 12. Ten μl of the toxin dilutions are then added to the respective wells of a 96-well flat-bottom plate containing 50,000 Sup-T1 cells per well. Following incubation for 6 hours at 37° C., 10 μl cell-counting kit-8 reagent (Dojindo Labs, Gaithersburg, Md.) is added to the cells and incubated overnight at 37° C. The following day, the plate is placed on a spectrophotometric plate reader and read at A450. To determine the amount of toxin required to lyse 50% of the Sup-TI cells (LD50), the A450 values are plotted against amount toxin for each protein to produce a linear graph. The LD50 is determined by finding the amount toxin when the A450 value is half of its maximum value. The maximum A450 value is determined from control lanes containing cells without toxin. This is an alternative assay, for testing lytic activity of the mutant versus the wild-type toxin.

Activation and Oligomerization Assay

Activation of $AT^{pro}$ was accomplished using trypsin at 1:3500 (w/w) trypsin to toxin ratio. The trypsin and toxin were incubated at 37° C. for 30 min. The reaction was stopped with the addition of a 30-fold molar excess of the protease inhibitor TLCK. The reactions were then run on a 10% SDS-PAGE gel and blotted onto nitrocellulose. The blots were probed with affinity-purified anti-AT antibody and a secondary antibody conjugated to alkaline phophatase for calorimetric development. The blots were then checked for the presence of protoxin, activated toxin and oligomerized toxin.

It is important to determine that the mutant still maintains the conformational integrity and structure of the native alpha toxin protein, and that any loss of activity in the mutant is due solely to the specific substitution or deletion and not to a change in conformation or structured integrity. All mutants, point substitutions and deletions, were tested for structural integrity by trypsin activation and oligomerizaion. If the structure of the mutant protein remains intact, the propeptide should be removed and the protein should oligomerize in the presence of trypsin. All mutants so tested have been tested and found to be structurally sound.

TABLE II

| Mutant ID | Position in SEQ ID NO: 3 | HA Average | hFR Binding | SUPT1 Binding |
|---|---|---|---|---|
| Wild Type | | 100 | 100 | 100 |
| W85A | 53 | 70.08 | 86.83 | 53.9 |
| C86L | 54 | 0 | 0 | 0 |
| V94A | 62 | 23.3 | 0 | 0 |
| Loop #1 | | | | |
| R117A | 85 | 77.18 | 38.23 | 81.82 |
| Y118T | 86 | 17 | 18.62 | 100 |
| N119A | 87 | 63.88 | 67.04 | 36 |
| N121A | 89 | 64.76 | 94.41 | 75 |
| D122A | 90 | 15.82 | 0 | 32.11 |
| Y124T | 92 | 13.87 | 0 | 17.2 |
| S126A | 94 | 64.26 | 94.15 | 29.03 |
| Y128T | 96 | 1.52 | 0 | 0 |
| R129A | 97 | 14.91 | 0 | 15.87 |

TABLE II-continued

| Mutant ID | Position in SEQ ID NO: 3 | HA Average | hFR Binding | SUPT1 Binding |
|---|---|---|---|---|
| K131A | 99 | 71.75 | 97.31 | 23.65 |
| D132A | 100 | 54.4 | 41.29 | 42.82 |
| R133A | 101 | 0 | 0 | 0 |
| L134A | 102 | 28.46 | 14.01 | 25 |
| Loop #2 | | | | |
| L291A | 259 | 1.64 | 0 | 0 |
| R292A | 260 | 2.37 | 8.16 | 0 |
| Y293T | 261 | 0.5 | 14.98 | 0 |
| T294A | 262 | 28.81 | 27.31 | 19.29 |
| N296A | 264 | 0 | 0 | 0 |
| R298A | 266 | 4.19 | 0 | 0 |
| E299A | 267 | 90.42 | 72.42 | 57.89 |
| D300A | 268 | 0 | 0 | 14.4 |
| H301A | 269 | 0 | 0 | 0 |
| T302A | 270 | 12.5 | 9.95 | 23.89 |
| E303A | 271 | 85.92 | 83.89 | 71.05 |
| D304A | 272 | 83.76 | 103.13 | 67.5 |
| R305A | 273 | 0 | 0 | 0 |
| Helix | | | | |
| W342A | 310 | 0 | 0 | 0 |

Table II. Hemolytic activity, hFR binding activity and Sup-T1 cell binding activity of *C. septicum* mutants with amino acid substitutions in receptor binding sites. Activity is percent of activity of wild type (native) *C. septicum* alpha toxin.

UTILITY

In a preferred use, the invention contemplates a vaccine for use in immunizing a human or an animal against an infection by *C. septicum*, the vaccine comprising any one or more of the purified *C. septicum* alpha toxin mutants described herein which can induce an immune response. The present invention further comprises a method of immunizing a human or an animal against an infection by *C. septicum*, by administering an effective amount of a vaccine comprising at least one purified *C. septicum* alpha toxin mutant as defined elsewhere herein, wherein the amount is effective in stimulating an immune response in the subject. In this method, the vaccine may be administered by epicutaneous injection, subcutaneous injection, intramuscular injection, interdermal injection, intravenous injection, sustained-release repository, aerosolization, parenteral delivery, or inoculation into an egg. In one embodiment of the method, the vaccine induces an effective antibody titer to prevent or eliminate the infection without administration of a booster of the vaccine.

The present invention further contemplates a serum for treating a subject with a *C. septicum* infection comprising polyclonal or monoclonal antibodies against a *C. septicum* alpha toxin wherein the antibodies are raised against a *C. septicum* alpha toxin mutant as defined elsewhere herein.

The present invention further contemplates a polyclonal or monoclonal antibody against a *C. septicum* alpha toxin wherein said antibody is raised against a *C. septicum* alpha toxin mutant as defined elsewhere herein. The present invention further contemplates a method of treating a human or animal having, or disposed to having, a *C. septicum* infection, comprising administering to the subject a therapeutically effective amount of an antibody to an alpha toxin of *C. septicum*, the antibody raised against a *C. septicum* alpha toxin mutant as defined elsewhere herein. The method for treating a *C. septicum* infection may comprise administering a serum comprising monoclonal or polyclonal antibodies effective against *C. septicum* alpha toxin.

The administration of a human or animal vaccine in accordance with the present invention is generally applicable to the prevention or treatment of *C. septicum* disease. The vaccine may be administered by epicutaneous injection, subcutaneous injection, intramuscular injection, interdermal injection (injection by infusion), sustained-release repository, aerosolization, parenteral delivery, inoculation into an egg, and the like, by known techniques in the art. Although this approach is generally satisfactory, other routes of administration, such as i.v. (into the blood stream) may also be used in a manner known to those of ordinary skill in the art. In addition, the vaccine can be given together with adjuvants and/or immuno-modulators to boost the activity of the vaccine and the subject's response, the subject being a human or animal as described elsewhere herein.

The amount of protein in each vaccine dose can be selected as an amount which induces an immunoprotective response without significant, adverse side effects in typical vaccines. Such amount will vary depending upon which specific immunogen is employed, how it is presented, and the size and species of the subject treated. Generally, it is expected that each dose will comprise 0.1–1000 µg/kg of weight of the subject, preferably 0.2–100 µg/kg, and most preferably 1–10 µg/kg. An optimal amount for a particular vaccine can be ascertained by standard studies involving observation of appropriate immune responses in subjects. Following an initial vaccination, subjects may receive one or several booster immunization adequately spaced.

Accordingly in one aspect, the invention provides a method of treatment comprising administering an effective amount of a vaccine of the present invention to a subject. The vaccine formulations of the present invention may be used for both prophylactic and therapeutic purposes. The vaccine compositions of the present invention can be formulated according to known methods of preparing pharmaceutically useful compositions, whereby these materials are combined in a mixture with a pharmaceutically acceptable carrier vehicle. Suitable vehicles and their formulation are described, for example, in *Remington's Pharmaceutical Sciences*,(2000, 20$^{th}$ Ed.).

The alpha toxin mutants are preferably administered as a composition in combination with a pharmaceutical carrier compatible with the protein and the subject. Suitable pharmacological carriers include, for example, physiological saline (0.85 %), phosphate-buffered saline (PBS), Tris hydroxymethyl aminomethane (TRIS), Tris-buffered saline, and the like. The mutant may also be incorporated into a carrier which is biocompatible and can incorporate the protein and provide for its controlled release or delivery, for example, a sustained release polymer such as a hydrogel, acrylate, polylactide, polycaprolactone, polyglycolide, or copolymer thereof. An example of a solid matrix for implantation into the subject and sustained release of the protein antigen into the body is a metabolizable matrix, as known in the art.

Adjuvants may be included in the vaccine to enhance the immune response in the subject. Such adjuvants include, for example, aluminum hydroxide, aluminum phosphate, Freund's Incomplete Adjuvant (FCA), liposomes, ISCOM, and the like. The vaccine may also include additives such as buffers and preservatives to maintain isotonicity, physiological pH and stability. Parenteral and intravenous formulations of the vaccine may include an emulsifying and/or suspending agent, together with pharmaceutically-acceptable diluents to control the delivery and the dose amount of the vaccine.

Factors bearing on the vaccine dosage include, for example, the age, weight, and species of the subject. The range of a given dose is about 25–5000 µg of the purified mutant receptor protein per ml, preferable about 100–1000 µg/ml preferably given in about 0.1–5 ml doses. The vaccine should be administered to the subject in an amount effective to ensure that the subject will develop an immunity to protect against a C. septicum infection or alpha toxin produced thereby. For example, a vaccine for immunizing an about 5-lb. piglet against C. septicum would contain about 100–5000 µg protein per ml, preferably given in 1–5 ml doses. The immunizing dose would then be followed by a booster given at about 21–28 days after the first injection. Preferably, the vaccine is formulated with an amount of the alpha toxin mutant effective for immunizing a susceptible subject against an infection by more than one strain C. septicum.

The present invention further contemplates monoclonal or polyclonal antibodies raised against one or more C. septicum alpha toxin mutants. The antibody may be prepared by a method comprising immunizing a suitable animal or animal cell with an immunogenic C. septicum alpha toxin mutant to obtain cells for producing an antibody to said mutant, fusing cells producing the antibody with cells of a suitable cell line, and selecting and cloning the resulting cells producing said antibody, or immortalizing an unfused cell line producing said antibody, e.g. by viral transformation, followed by growing the cells in a suitable medium to produce said antibody and harvesting the antibody from the growth medium in a manner well known to those of ordinary skill in the art. The recovery of the polyclonal or monoclonal antibodies may be preformed by conventional procedures well known in the art, for example as described in Kohler and Milstein, *Nature* 256, 1975, p. 495.

The antisera of the invention are readily prepared by injecting a host animal (e.g. a mouse, pig or rabbit) with a mutant of the invention and then isolating serum from it after a waiting suitable period for antibody production, e.g. 14 to 28 days. Antibodies may be isolated from the blood of the animal or its sera by use of any suitable known method, e.g. by affinity chomatography using immobilized mutants of the invention or the mutants they are conjugated to, e.g. GST, to retain the antibodies. Similarly monoclonal antibodies may be readily prepared using known procedures to produce hybridoma cell lines expressing antibodies to peptides of the invention. Such monoclonals antibodies may also be humanized e.g. using further known procedures which incorporate mouse monoclonal antibody light chains from antibodies raised to the mutants of the present invention with human antibody heavy chains.

In a further aspect, the invention relates to a diagnostic agent which comprises a monoclonal antibody as defined above. Although in some cases when the diagnostic agent is to be employed in an agglutination assay in which solid particles to which the antibody is coupled agglutinate in the presence of a C. septicum toxin in the sample subjected to testing, no labeling of the monoclonal antibody is necessary, it is preferred for most purposes to provide the antibody with a label in order to detect bound antibody. In a double antibody ("sandwich") assay, at least one of the antibodies may be provided with a label. Substances useful as labels in the present context may be selected from enzymes, fluorescers, radioactive isotopes and complexing agents such as biotin. In a preferred embodiment, the diagnostic agent comprises at least one antibody covalently or non-covalently bonded coupled to a solid support. This may be used in a double antibody assay in which case the antibody coupled to the solid support is not labeled. The solid support may be selected from a plastic, e.g. latex, polystyrene, polyvinylchloride, nylon, polyvinylidene difluoride, cellulose, e.g. nitrocellulose and magnetic carrier particles such as iron particle coated with polystyrene.

The monoclonal antibody of the invention may be used in a method of determining the presence of C. septicum alpha toxin in a sample, the method comprising incubating the sample with a monoclonal antibody as described above and detecting the presence of bound toxin resulting from said incubation. The antibody may be provided with a label as explained above and/or may be bound to a solid support as exemplified above.

In a preferred embodiment of the method, a sample desired to be tested for the presence of C. septicum is incubated with a first monoclonal antibody coupled to a solid support and subsequently with a second monoclonal or polyclonal antibody provided with a label. In an alternative embodiment (a so-called competitive binding assay), the sample may be incubated with a monoclonal antibody coupled to a solid support and simultaneously or subsequently with a labeled C. septicum alpha toxin competing for binding sites on the antibody with any toxin present in the sample. The sample subjected to the present method may be any sample suspected of containing a C. septicum alpha toxin. Thus, the sample may be selected from bacterial suspensions, bacterial extracts, culture supernatants, animal body fluids (e.g. serum, colostrum or nasal mucous) and intermediate or final vaccine products.

Apart from the diagnostic use of the monoclonal antibody of the invention, it is contemplated to utilize a well-known ability of certain monoclonal antibodies to inhibit or block the activity of biologically active antigens by incorporating the monoclonal antibody in a composition for the passive immunization of a subject against diseases caused by C. septicum producing an alpha toxin, which comprises a monoclonal antibody as described above and a suitable carrier or vehicle. The composition may be prepared by combining a therapeutically effective amount of the antibody or fragment thereof with a suitable carrier or vehicle. Examples of suitable carriers and vehicles may be the ones discussed above in connection with the vaccine of the invention. It is contemplated that a C. septicum -specific antibody may be used for prophylactic or therapeutic treatment of a subject having a C. septicum infection or a subject which may potentially incur a C. septicum infection.

A further use of the monoclonal antibody of the invention is in a method of isolating a C. septicum alpha toxin, the method comprising adsorbing a biological material containing said toxin to a matrix comprising an immobilized monoclonal antibody as described above, eluting said toxin from said matrix and recovering said toxin from the eluate. The matrix may be composed of any suitable material usually employed for affinity chromatographic purposes such as agarose, dextran, controlled pore glass, DEAE cellulose, optionally activated by means of CNBr, divinylsulphone, etc. in a manner known per se.

In a still further aspect, the present invention relates to a method of determining the presence of antibodies against C. septicum alpha toxin in a sample, the method comprising incubating the sample with C. septicum alpha toxin and detecting the presence of bound antibody resulting from incubation. A diagnostic agent comprising the alpha toxin used in this method may otherwise exhibit any of the features described above for diagnostic agents comprising the monoclonal antibody and be used in similar detection methods although these will detect bound antibody rather than bound alpha toxin as such. The diagnostic agent may be useful, for instance as a reference standard or to detect anti-toxin antibodies in body fluids, e.g. serum, colostrum or nasal mucous, from subjects exposed to the toxin or *C. septicum*.

The monoclonal antibody of the invention may be used in a method of determining the presence of a *C. septicum* toxin, in a sample, the method comprising incubating the sample with a monoclonal antibody and detecting the presence of bound toxin resulting from said incubation.

The various mutants of alpha toxin that exhibit various degrees of hemolytic activity as a result in a change in receptor binding, membrane insertion or oligomerization, may be used as standards in a hemolytic assay. In such cases different mutants could be used to act as standards that would exhibit different hemolytic activity at the same concentrations. For example, mutants exhibiting 0, 25, 50 and 75% of the activity of the wild-type alpha toxin could be used in a hemolytic assay as described elsewhere herein to provide standards to which mutants of unknown activity could be compared. One advantage of this approach would be that although the hemolytic activity would vary, the protein concentration would not and therefore any differences due to the denaturation of protein when diluted would be eliminated. Hence, all mutants for which hemolytic activity was known could be compared at the same concentration to these standards for an estimate of their hemolytic activity.

The present invention further contemplates a nucleic acid sequence encoding any of the *C. septicum* alpha toxin mutants as described herein wherein the nucleic acid sequence is a cDNA similar to a cDNA which encodes native *C. septicum* alpha toxin, but differs therefrom only in having instead one or more substituted codons and/or codon deletions which encodes the one or more substituted amino acids and/or deleted amino acids, respectively, in the mutant alpha toxin, as defined elsewhere herein, and wherein the substituted codon is any codon known to encode the substitute amino acid residue. The mutant alpha toxin described herein may be produced by well-known recombinant methods using cDNA encoding the mutant alpha toxin, the cDNA having been transfected into a host cell in a plasmid or other vector.

It is clear from the above that the present invention provides compositions and methods for the production of *C. septicum* alpha toxin mutants. Indeed, from the above it is clear that the present invention provides compositions and methods suitable for the preparation of effective multivalent vaccines, and antibodies against alpha toxin, as well as preparations suitable for use in the treatment of various conditions induced by infection with *C. septicum*.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should no be unduly limited to such specific embodiments. Indeed, various modifications of the described modes for carrying out the invention which are obvious to those skilled in molecular biology or related fields are intended to be within the scope of the following claims.

---

What is claimed is:

1. A mutant of *C. septicum* alpha toxin polypeptide, comprising:
SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23.

* * * * *

UNITED STATES PATENT AND TRADEMARK OFFICE
CERTIFICATE OF CORRECTION

PATENT NO. : 7,179,888 B2  
APPLICATION NO. : 10/194489  
DATED : February 20, 2007  
INVENTOR(S) : Rodney K. Tweten and Jody Melton It is certified that error appears in the above-identified patent and that said Letters Patent is hereby corrected as shown below:

In the Specification:
Column 2, line 64: Delete "gluat313," and replace with -- glu at 313, --

Column 10, lines 2, 5, 8, 11, 14 & 17: After "pro," delete "gin," and replace with -- gln --

Column 11, lines 30, 33, 36, 39, 42 & 45: After "pro," delete "gin," and replace with -- gln --

Column 14, line 35: Delete "calorimetric" and replace with -- colorimetric --

Column 14, line 39: Delete "confornational" and replace with -- conformational --

Signed and Sealed this

Twenty-second Day of May, 2007

JON W. DUDAS  
*Director of the United States Patent and Trademark Office*

UNITED STATES PATENT AND TRADEMARK OFFICE
CERTIFICATE OF CORRECTION

PATENT NO. : 7,179,888 B2
APPLICATION NO. : 10/194489
DATED : February 20, 2007
INVENTOR(S) : Rodney K. Tweten and Jody Melton It is certified that error appears in the above-identified patent and that said Letters Patent is hereby corrected as shown below:

In the Claims:

Column 81, lines 41-45 and Column 82, lines 39-41: Delete in entirety Claim 1 and replace with -- 1. A mutant of Clostridium septicum alpha toxin polypeptide comprising the sequence set forth in SEQ ID NO: 17 wherein the amino acid at position 269 is selected from the group consisting of alanine, cysteine, aspartate, glutamate, phenylalanine, glycine, isoleucine, lysine, leucine, methionine, asparagine, proline, glutamine, arginine, serine, threonine, valine, tryptophan and tyrosine. --

Signed and Sealed this

Twenty-second Day of December, 2009

David J. Kappos
*Director of the United States Patent and Trademark Office*